United States Patent
Suzuki et al.

(10) Patent No.: US 7,053,997 B2
(45) Date of Patent: May 30, 2006

(54) METHOD OF OBTAINING PARTICULARS OF OPHTHALMIC LENS

(75) Inventors: Hiroaki Suzuki, Toki (JP); Kazuhiko Nakada, Nisshin (JP)

(73) Assignee: Menicon Co., Ltd., Nagoya (JP)

( * ) Notice: Subject to any disclaimer, the term of this patent is extended or adjusted under 35 U.S.C. 154(b) by 982 days.

(21) Appl. No.: 10/053,744

(22) Filed: Jan. 23, 2002

(65) Prior Publication Data

US 2002/0146161 A1  Oct. 10, 2002

(30) Foreign Application Priority Data

| Jan. 23, 2001 | (JP) | ............... 2001-014031 |
| Feb. 13, 2001 | (JP) | ............... 2001-035126 |
| Feb. 21, 2001 | (JP) | ............... 2001-044758 |

(51) Int. Cl.
 G01B 9/00 (2006.01)
 G01N 21/64 (2006.01)

(52) U.S. Cl. ................ 356/124; 250/459.1; 250/461.1

(58) Field of Classification Search ......... 356/124–127
 See application file for complete search history.

(56) References Cited

U.S. PATENT DOCUMENTS

| 4,238,524 A | 12/1980 | LaLiberte et al. |
| 4,303,701 A | 12/1981 | Torgersen et al. |
| 4,615,593 A | 10/1986 | Neefe |
| 4,695,399 A | 9/1987 | Neefe |
| 5,521,657 A | 5/1996 | Klopotek |
| 5,633,504 A | 5/1997 | Collins et al. |
| 6,124,594 A | 9/2000 | Duggan et al. |

FOREIGN PATENT DOCUMENTS

| EP | 0 402 825 A1 | 12/1990 |
| JP | 02-116731 | 5/1990 |
| JP | 9-504095 | 4/1997 |
| JP | 11-503232 | 3/1999 |
| JP | 2000-177720 | 6/2000 |
| KR | 8302248 A1 | 10/1983 |
| WO | WO 95/04264 | 2/1995 |

*Primary Examiner*—Samuel A. Turner
*Assistant Examiner*—Amanda Merlino
(74) *Attorney, Agent, or Firm*—Burr & Brown

(57) ABSTRACT

A method of obtaining particulars or characteristics of an ophthalmic lens by detecting a fluorescent light which is emitted from the ophthalmic lens upon exposure to an excitation light (UV light). The particulars or characteristics of the ophthalmic lens include, for instance, identifying marks such as characters, figures, symbols, etc. which are formed in the ophthalmic lens to identify the ophthalmic lens, a thickness of the ophthalmic lens such as a contact lens and an intraocular lens, and an angular position of the ophthalmic lens, particularly of a special contact lens having circumferential portions having respective different thickness values.

6 Claims, 13 Drawing Sheets

⇒ REFERENCE RADIAL DIRECTION

↗ REFERENCE RADIAL DIRECTION

METHOD OF OBTAINING PARTICULARS OF OPHTHALMIC LENS

This application is based on Japanese Patent Application Nos. 2001-014031 filed on Jan. 23, 2001, 2001-035126 filed on Feb. 13, 2001, and 2001-044758 filed on Feb. 21, 2001, the contents of which are incorporated hereinto by reference.

BACKGROUND OF THE INVENTION

1. Field of the Invention

The present invention relates in general to a method of obtaining particulars or characteristics of an ophthalmic lens by detecting a fluorescent light which is emitted from the ophthalmic lens upon exposure to an excitation light (UV light). The particulars or characteristics of the ophthalmic lens include, for instance, identifying marks such as characters, figures, symbols, etc. which are formed in the ophthalmic lens to identify the ophthalmic lens, a thickness of the ophthalmic lens such as a contact lens and an intraocular lens, and an angular position of the ophthalmic lens, particularly of a special contact lens having circumferential portions having respective different thickness values.

2. Discussion of Related Art

As one example of the particulars or characteristics of an ophthalmic lens which give information on the lens, there are known identifying marks formed in predetermined portions of the ophthalmic lens such as a contact lens or an intraocular lens. The identifying marks include characters, figures, symbols and others, which permit or facilitate a differentiation between front and back surfaces of the lens or between lenses for left and right eyes. Further, the identifying marks are formed to indicate the thickest circumferential portion in the lens or specifications of the lens and manufacturing information such as a manufacturer's name. For marking the ophthalmic lens, a laser radiation is used to engrave the identifying marks in the lens surface, or a printing liquid containing a pigment or a dye is used.

The identifying marks formed in the ophthalmic lens as described above are checked or read upon packaging or shipment of the lens by a worker, for assuring delivery of a lens suitable to a specific user, or distinguishing various types of lenses from each other in the production line. In general, the identifying marks are manually checked by the worker for each of a plurality of ophthalmic lenses, by visually inspecting each lens directly or through a magnifying glass. Since the identifying marks are formed generally at a peripheral portion of the lens for the purpose of avoiding an adverse influence on its optical region, it is rather difficult to recognize the identifying marks by the worker's visual inspection. Accordingly, the conventional method of reading the identifying marks by the worker's visual inspection undesirably suffers from reading errors of the identifying marks due to sensory errors and fatigue of individual workers. Further, the production efficiency of the lens is undesirably deteriorated.

In view of a current trend that disposable contact lenses are widely used, there is a demand for mass-production of the ophthalmic lens with high production efficiency at a reduced cost. The above-described conventional method of manually reading the identifying marks by the worker's visual inspection, however, does not meet the demand.

As one technique for solving the problem described above, it is proposed to take an image of the marked ophthalmic lens by a CCD camera, for instance, and to process the obtained image by an image data processing device. In this technique, however, it is difficult to obtain a sufficiently clear image of the lens for reading the identifying marks since the ophthalmic lens is transparent and the identifying marks formed in the lens are transparent or pale in color.

U.S. Pat. No. 6,124,594 discloses a method of confirming the presence of a contact lens in a package by using an infrared radiation. JP-A-2000-177720, JP-A-11-503232, and JP-A- 9-504095 disclose a method of detecting the presence of a contact lens in a container, or a method of detecting defects of a contact lens such as scratches and chips, comprising the steps of applying an excitation light such as a UV light to the contact lens, and taking a fluorescent image of the lens while the lens is emitting a fluorescent light by exposure to the excitation light. None of the methods, however, disclose or suggest reading the identifying mark formed in the lens by utilizing the fluorescent image. Accordingly, the identifying mark needs to be read manually by the worker's visual inspection, thereby causing a risk of delivering, to a user, improper lenses having the specifications such as the optical power and the radius of curvature, which are different from those suitable to a specific lens user.

It is therefore a first object of the present invention to provide a method of accurately and easily reading an identifying mark formed in an ophthalmic lens so as to obtain information on the lens, so that the obtained information are compared with prepared reference information for the purpose of distinguishing various types of lenses from each other in the production line.

Another example of the particulars which give information on the ophthalmic lens, the thickness of the ophthalmic lens, especially at its optical center, is measured. For providing a lens user with an ophthalmic lens suitable to an eye of the lens user, and for effectively practicing a quality inspection and an inventory control of the ophthalmic lens, it is required to measure the optical center thickness of the ophthalmic lens. There are proposed various methods for measuring the optical center thickness of the ophthalmic lens, especially a contact lens, for example, methods which use contact members, an ultrasonic wave, and an optical microscope.

For instance, a dial gauge or indicator which includes a pair of contact members is used for measuring the optical center thickness of the ophthalmic lens. The contact members are brought into contact with central portions of the opposite surfaces of the ophthalmic lens, respectively, so that the optical center thickness of the ophthalmic lens between the contact members is measured. In this contact-type method wherein the contact members are held in contact with the ophthalmic lens, there is a risk that the contact members may scratch or damage the ophthalmic lens surface. Further, since it is difficult to accurately determine a position of the lens at which the thickness should be measured, the thickness cannot be measured at a desired portion every time when the ophthalmic lens is subjected to the measuring operation, undesirably causing measuring errors. Where the contact members having a relatively large diameter are used to measure the optical center thickness of a toric lens or a bifocal lens whose optical center is offset from a geometrical center, it is difficult to bring the contact members into accurate abutting contact with the desired circumferential portion of the lens whose thickness varies in the circumferential direction. In this case, the optical center thickness of the ophthalmic lens cannot be accurately measured.

When the optical center thickness of the ophthalmic lens is measured by using the ultrasonic wave, the ultrasonic wave generated from an ultrasonic wave transducer is applied to the ophthalmic lens along an axis passing the center of the spherical surface of the lens. The optical center thickness of the ophthalmic lens is obtained from the waves which are respectively reflected by the opposite surfaces of the lens. Unlike the above-described method using the contact members, this method permits the measurement of the optical center thickness of the lens in a non-contact manner without using any members in contact with the lens surface. This method, however, requires a relatively long period of time for the thickness measurement and an accurate temperature control, inevitably pushing up the cost of the measuring device.

When the optical center thickness is measured by using the optical microscope, it is generally impossible to measure the thickness of the ophthalmic lens with the lens being immersed in a liquid such as water, due to attenuation of a light. A soft contact lens, in particular, is likely to be deformed due to evaporation of the aqueous component therefrom during the measuring operation, whereby the thickness of the lens cannot be accurately measured.

It is therefore a second object of the present invention to provide a novel method of easily and accurately obtaining a thickness of an ophthalmic lens in a non-contact manner without using any members in contact with the lens surface, for thereby avoiding a risk of damaging the ophthalmic lens.

As another example of the particulars which give information on the ophthalmic lens, an angular position of the ophthalmic lens is detected. The angular portion of the ophthalmic lens is detected for the following reasons.

As a contact lens for vision correction of an eye suffering from deteriorated accommodation such as presbyopia and astigmatism, there is proposed a special contact lens having circumferential portions having respective different thickness values. The special contact lens includes a toric lens having a toric shape, and a multifocal lens such as a bifocal lens having a plurality of vision correction powers.

The special contact lens such as the astigmatism correction contact lens or the presbyopia correction contact lens providing near and distant vision correction powers is positioned on an eye of the lens wearer with a predetermined circumferential orientation thereon while being prevented from rotating in the circumferential direction. As one technique for positioning the lens on the lens wearer's eye with a predetermined circumferential orientation, a prism ballast mechanism is generally known. The contact lens which employs the prism ballast mechanism has a gravity center at a relatively lower portion thereof, by offsetting the centers of front and back surfaces from each other by a suitable offset amount, with the thickness of the lower portion being increased. Therefore, the contact lens can be placed on the eye while maintaining the desired circumferential orientation. In the contact lens with the prism ballast mechanism described above, the lower portion thereof has a thickness larger than the other portion when placed on the eye with the desired circumferential orientation.

For an effective quality inspection and an inventory control of the special contact lens described above, there are conducted various examinations on the special contact lens for obtaining the characteristics thereof. In the astigmatism correction contact lens, for instance, a spherical power, a cylindrical power, an orientation of an astigmatic axis, and an amount of prism are examined. The presbyopia correction contact lens is examined, for instance, for the circumferential positions of areas or regions to which a distant and a near vision correction power and an additional power are given.

Prior to these examinations, it is necessary to clarify or specify a position of a reference circumferential portion at which the thickness of the lens is the largest. In other words, it is necessary to detect a reference radial direction which is defined by a geometrical center of the lens and the reference circumferential portion having the largest thickness.

For detecting the reference radial direction described above, a suitable index or a mark is formed on the surface of the special contact lens at a circumferential position corresponding to the reference circumferential portion having the largest thickness. In conducting various examinations, the index of the lens is positioned in the circumferential direction with a suitable inspecting device. However, the manual positioning of the index of the contact lens with the inspecting device inevitably causes a positioning error, and requires a relatively long period of time for detecting the reference radial direction.

Even if the reference radial direction were appropriately recognized, the cost of producing the contact lens would be undesirably increased due to forming the index on the lens surface. Further, if the index is erroneously positioned on the lens surface, that is, the index is offset from the actual reference portion, the reference radial direction is inevitably determined based on the erroneously positioned index.

It is therefore a third object of the present invention to provide a novel method of easily and accurately detecting an angular position of an ophthalmic lens, particularly, a special contact lens having different thickness values at different circumferential positions, without forming any identifying marks or indices on the surface of the lens. The angular position of the lens is defined, for instance, by a position of the thickest circumferential portion (the above-described reference circumferential portion) of the lens, i.e., the reference radial direction.

SUMMARY OF THE INVENTION

As a result of an intensive study made by the inventors of the present invention in an effort to achieve the above-indicated first object of the invention relating to the method of reading the identifying mark, it was found that an image of the ophthalmic lens, which clearly represents the identifying mark, can be obtained by taking a fluorescent image of the lens by detecting a self-fluorescent light emitted from the lens upon irradiation with an excitation light, rather than directly taking an image of the ophthalmic lens.

The above-indicated first object of the invention may be achieved according to a first aspect of the invention, which provides a method of reading an identifying mark in the form of a character, a figure, or a symbol, which is formed in a predetermined portion of a surface of an ophthalmic lens and which identifies the ophthalmic lens, comprising the steps of: irradiating the ophthalmic lens with an excitation light so that a self-fluorescent light is emitted from the ophthalmic lens; taking a fluorescent image of the ophthalmic lens while the ophthalmic lens is emitting the self-fluorescent light; obtaining information on the ophthalmic lens by reading the identifying mark formed in the ophthalmic lens, on the basis of the fluorescent image.

In the present method of reading the identifying mark formed in the ophthalmic lens, the ophthalmic lens is irradiated with a suitable excitation light, and the fluorescent image of the lens is obtained by detecting the self-fluorescent light over the entire surface of the lens, which self-fluorescent light is emitted from the material of the lens by exposure to the excitation light. The thus obtained fluorescent image of the lens represents the identifying mark formed in the lens with higher clarity than an image of the lens which is directly taken by a camera. According to the present method, the identifying mark formed in the ophthalmic lens can be considerably easily read or recognized, so that the information on the ophthalmic lens can be advantageously obtained.

Since the identifying mark is clearly represented by the fluorescent image of the lens, the identifying mark can be automatically read or recognized by a suitable system, for thereby permitting a quick and continuous reading of the identifying mark of each of the mass-produced ophthalmic lenses, and significantly reducing a labor cost required for reading the identifying mark, which results in a reduction of the manufacturing cost of the ophthalmic lens.

In a preferred form of the above-described first aspect of the invention, the method further comprises a step of judging whether the obtained information is identical with prepared reference information. This arrangement effectively avoids the conventionally experienced problem of delivering, to a user, an improper lens having specifications not suitable to the specific user. Further, the mass-produced ophthalmic lenses having respective different specifications can be effectively distinguished from one another in the production line.

In another preferred form of the above-indicated first aspect of the invention, the step of irradiating the ophthalmic lens with an excitation light and said step of taking a fluorescent image are effected with the ophthalmic lens being immersed in a liquid medium accommodated in a container. Since the identifying mark formed in the ophthalmic lens can be read while the ophthalmic lens is immersed in the liquid medium, the ophthalmic lens, especially, a hydrogel or water-swollen lens is protected from being dried, so that the lens does not suffer from any deformation due to evaporation of the aqueous component therefrom.

In still another preferred form of the above-indicated first aspect of the invention, the step of taking a fluorescent image of the ophthalmic lens is effected by using a CCD camera. According to this arrangement, the fluorescent image can be effectively obtained.

The excitation light which irradiates the ophthalmic lens is preferably a UV light having a wavelength in a range of 200–400 nm, and the fluorescent light emitted from the ophthalmic lens preferably has a wavelength in a range of 340–470 nm. Accordingly, the fluorescent image can be obtained with high accuracy, so that the identifying mark can be effectively read.

To attain the above-indicated second object of the invention relating to the method of obtaining the thickness of the ophthalmic lens, the inventors of the present invention made an intensive study and found that there is a predetermined correlation, irrespective of the curvature of the lens surface, between the thickness of the ophthalmic lens and the luminance of the self-fluorescent light emitted from the material of the lens by exposure to the excitation light,.

The second object indicated above may be achieved according to a second aspect of the invention, which provides a method of obtaining a thickness of an ophthalmic lens, comprising the steps of irradiating the ophthalmic lens with an excitation light so that a self-fluorescent light is emitted from the ophthalmic lens; obtaining a luminance value at a thickness measuring portion of the ophthalmic lens from the self-fluorescent light; and determining the thickness at the thickness measuring portion on the basis of the obtained luminance value and according to a predetermined relationship between the thickness of the thickness measuring portion and the luminance value of the self-fluorescent light generated by irradiation with the excitation light.

In the present method described above, the self-fluorescent light which is emitted from the ophthalmic lens upon irradiation with a suitable excitation light is detected over the entire surface of the ophthalmic lens or at a desired portion thereof. It is considered that the ophthalmic lens emits a fluorescent light owing to transition of the electrons of the molecules of the ophthalmic lens material. From the detected fluorescent light, the luminance value at the thickness measuring portion is obtained, and the thickness of the thickness measuring portion is determined on the basis of the obtained luminance value and according to the predetermined relationship between the thickness of the thickness measuring portion and the luminance value of the self-florescent light. The relationship is represented by a calibration curve, for instance. According to this method, the thickness of the ophthalmic lens can be easily obtained in a non-contact manner without using the conventional contacting members which are held in contact with the opposite surfaces of the lens, so that the ophthalmic lens does not suffer from any damage. Further, the present method permits an accurate measurement of the optical center thickness of various lenses such as a mono-focal lens having the smallest thickness at its geometrical center, a toric or a bifocal lens having a thin-walled portion at its lower or upper portion, and other lenses whose optical center is offset from its geometrical center. The thickness of those lenses could not be accurately measured by the conventional method using the contact-type thickness measuring device.

In one preferred form of the above-indicated second aspect of the invention, the step of obtaining a luminance value at the thickness measuring portion comprises a step of taking a fluorescent image of the ophthalmic lens while the ophthalmic lens is emitting the self-fluorescent light, the fluorescent mage representing a distribution of luminance values on a surface of the ophthalmic lens irradiated with the excitation light, the luminance value at the thickness measuring portion being obtained on the basis of the distribution. According to this arrangement, the entire image of the fluorescing ophthalmic lens can be obtained, so that the position of the intended thickness measuring portion can be easily and accurately determined in the obtained fluorescent image of the lens. Further, the present arrangement permits the thickness to be measured at any desired portion of the lens.

In another preferred form of the above-indicated second aspect of the invention, the step of taking a fluorescent image of the ophthalmic lens is effected by using a CCD camera. According to this arrangement, the fluorescent image can be effectively obtained.

In still another preferred form of the above-indicated second aspect of the invention, the fluorescent image of the ophthalmic lens represents a distribution of different colors corresponding to respective values of luminance of local portions of the ophthalmic lens, the thickness of the thickness measuring portion being obtained from one of the different colors which corresponds to the thickness measuring portion. According to this arrangement, the luminance and the thickness of the ophthalmic lens can be easily obtained or recognized.

The excitation light which irradiates the ophthalmic lens is preferably a UV light having a wavelength in a range of 200–400 nm, and the fluorescent light emitted from the ophthalmic lens preferably has a wavelength in a range of 340–470 nm. Accordingly, the fluorescent image can be obtained with high accuracy.

To achieve the above-indicated third object of the invention relating to the method of detecting the angular position of the ophthalmic lens, the inventors of the present invention made an intensive study and found that the luminance of the self-fluorescent light emitted from the material of the ophthalmic lens upon exposure to the excitation light increases with an increase of the thickness of the ophthalmic lens. Further, it was found that the angular position of the ophthalmic lens such as a special contact lens having circumferential portions having respective different thickness values can be determined by detecting the self-fluorescent light emitted therefrom. The angular position of the ophthalmic lens is defined, for instance, by a position of the thickest circumferential portion of the lens, in other words, a reference radial direction which is defined by the geometrical center of the lens and the thickest circumferential portion of the lens. The thickest circumferential portion of the lens is aligned with the reference radial direction. Further, the angular position is also defined by a position of one of a near vision correction region and a distant vision correction region of the lens, in the circumferential direction.

The above-indicated third object of the invention may be achieved according to a third aspect of the invention, which provides a method of detecting an angular position of an ophthalmic lens having circumferential portions having respective different thickness values comprising the steps of irradiating the ophthalmic lens with an excitation light so that a self-fluorescent light is emitted from the ophthalmic lens; taking a fluorescent image of the ophthalmic lens while the ophthalmic lens is emitting the self-fluorescent light, the fluorescent image representing a distribution of luminance values on a surface of the ophthalmic lens irradiated with the excitation light; and determining the angular position of the ophthalmic lens on the basis of the distribution.

According to the method described above, the ophthalmic lens such as a special contact lens having circumferential portions having respective different thickness values by provision of the prism ballast mechanism, for instance, is irradiated with the excitation light, so that the self-fluorescent light is emitted from the ophthalmic lens. The self-fluorescent light is detected over the entire surface of the lens so as to provide a fluorescent image of the lens which represents a distribution of luminance values on the surface of the ophthalmic lens irradiated with the excitation light. It is considered that the ophthalmic lens emits a fluorescent light owing to transition of the electrons of the molecules of the ophthalmic lens material. Accordingly, the angular position of the ophthalmic lens can be easily and accurately detected or determined based on the distribution.

The present method permits an automatic and continuous detection of the angular position of each of a plurality of ophthalmic lenses, for thereby significantly reducing a required time and a labor cost for detecting the angular position of the ophthalmic lens.

In the present method wherein the self-fluorescent light emitted from the ophthalmic lens itself is detected, the detected fluorescent image of the ophthalmic lens has a considerably high degree of contrast, as compared with an image of an ophthalmic lens which is obtained by irradiating the lens with a visible light, and detecting a portion of the light which is reflected by the lens or which is not absorbed by the lens. Accordingly, the present method permits an accurate detection or determination of the angular position of the lens (e.g., the reference radial direction described above), which angular position could not be conventionally detected with high accuracy by detecting the light which is reflected by the lens or which is not absorbed by the lens.

In one preferred form of the above-indicated third aspect of the invention, the ophthalmic lens is a special contact lens which consists of an astigmatism correction contact lens or a presbyopia correction contact lens. If the present invention is applied to those lenses, the subsequent examination for obtaining various characteristics such as an optical power, an astigmatic axis orientation, an amount of prism, etc. can be accurately conducted.

In another preferred form of the above-indicated third aspect of the invention, the angular position is defined by a position of one of the thickest circumferential portion, a distant vision correction region, and a near vision correction region of the ophthalmic lens, in the circumferential direction.

In yet another preferred form of the above-indicated third aspect of the invention, the thickest circumferential portion is aligned with a reference radial direction which is defined as a radial direction extending from a geometrical center of the ophthalmic lens toward the thickest circumferential portion.

In still another preferred form of the above-indicated third aspect of the invention, the step of irradiating the ophthalmic lens with an excitation light and the step of taking a fluorescent image are effected with the ophthalmic lens being immersed in a liquid medium accommodated in a container.

In yet another preferred form of the above-indicated third aspect of the invention, the step of taking a fluorescent image is effected by using a CCD camera. According to this arrangement, the fluorescent image can be effectively obtained.

In a further preferred form of the above-indicated third aspect of the invention, the fluorescent image of the ophthalmic lens represents a distribution of different colors corresponding to respective values of luminance of local portions of the ophthalmic lens. According to this arrangement, the distribution of the luminance values of the ophthalmic lens can be easily recognized.

The excitation light which irradiates the ophthalmic lens is preferably a UV light having a wavelength in a range of 200–400 nm, and the fluorescent light emitted from the ophthalmic lens preferably has a wavelength in a range of 340–470 nm. According to this arrangement, the fluorescent image can be accurately detected, so that the angular position of the ophthalmic lens can be determined with high accuracy.

BRIEF DESCRIPTION OF THE DRAWINGS

The above and other objects, features, advantages and technical and industrial significance of the present invention will be better understood by reading the following detailed description of presently preferred embodiments of the invention, when considered in connection with the accompanying drawings, in which.

DETAILED DESCRIPTION OF PREFERRED EMBODIMENTS

Figure 1:
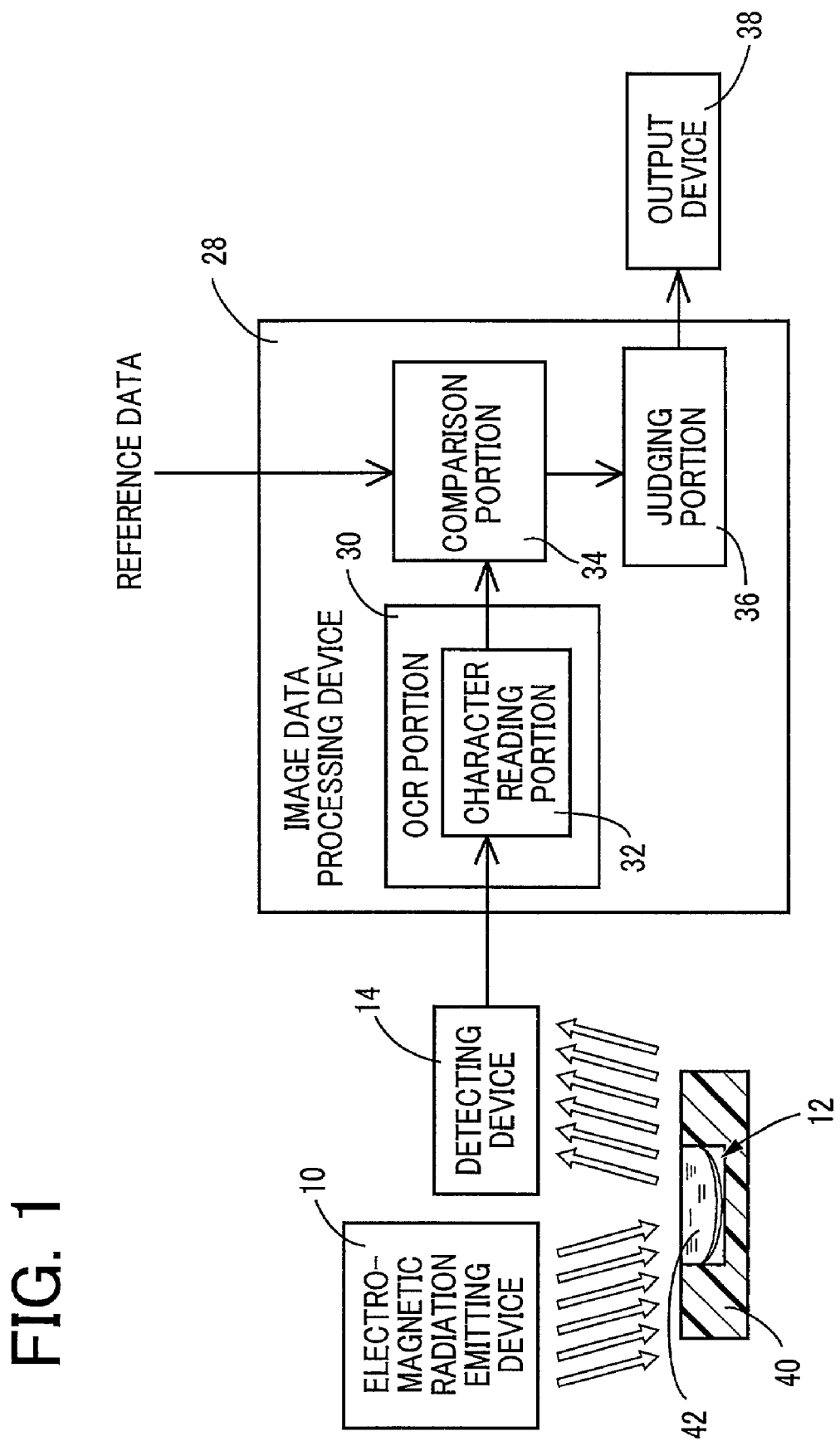
FIG. 1 is a schematic view showing one example of a reading device for reading the identifying mark formed in the ophthalmic lens, which device is constructed according to the present invention.

There will be described some embodiments of the present invention by referring to the drawings. In the present invention, a fluorescent light which is emitted from an ophthalmic lens by irradiation with an excitation light owing to excitation of the material of the ophthalmic lens is referred to as a self-fluorescent light.

Referring first to FIGS. 1–7, there will be described a first embodiment of the present invention, which is directed to a method of reading an identifying mark formed in an ophthalmic lens, as one example of the particulars or characteristics which give information on the ophthalmic lens. FIG. 1 schematically shows a reading device for reading the identifying mark formed in the ophthalmic lens. The reading device includes an electromagnetic radiation emitting device 10, a fluorescent image detecting device 14, an image data processing device 28, and an output device 38.

The electromagnetic radiation emitting device 10 emits a suitable light (an excitation light) having a predetermined wavelength, which is incident upon an ophthalmic lens with the identifying mark (marked ophthalmic lens), in the form of a marked contact lens 12 made of a known polymer material. The excitation light causes the marked contact lens 12 to emit a self-fluorescent light, owing to excitation of the polymer material of the marked contact lens 12. Any known light emitting device such as a xenon lamp, a mercury lamp, a deuterium lamp, a tungsten-iodine lamp, or a laser radiation emitting device is suitably employed as the electromagnetic radiation emitting device 10. The luminance or intensity of the fluorescent light which is emitted from the ophthalmic lens by exposure to the excitation light generally increases with an increase in the intensity of the excitation light. Although the luminance of the self-fluorescent light emitted from the ophthalmic lens is advantageously increased by application of the excitation light having a relatively high degree of intensity, it is needless to mention that the ophthalmic lens may suffer from an undesirable change in its quality due to exposure to the excitation light with an excessively high intensity.

The wavelength of the excitation light which irradiates the marked ophthalmic lens such as the marked contact lens 12 is not particularly limited, provided that the excitation light can generate the self-fluorescent light in the lens due to the excitation of the lens material itself. As the excitation light, a UV light having a wavelength in a range of 200–400 nm is preferably employed. The UV light may be a line spectrum of a narrow band width, a continuous spectrum of a relatively broad band width, or may be composed of a plurality of line spectra. The self-fluorescent light emitted from the marked ophthalmic lens by exposure to such a UV light is generally a light having a wavelength in a range of 340–470 nm.

For irradiating the marked contact lens 12 with the light in the desired wavelength range described above, an optical filter may be interposed between the electromagnetic radiation emitting device 10 and the marked contact lens 12. The optical filter is adapted to selectively pass therethrough only the excitation light in the desired wavelength range for exciting the material of the marked contact lens 12. Since the optical filter does not pass therethrough a light having a wavelength outside the desired range, the marked contact lens 12 can be effectively irradiated with the excitation light in the desired wavelength range emitted from the device 10.

The fluorescent image detecting device 14 takes two-dimensional fluorescent image of the marked contact lens 12 while the lens 12 is emitting the self-fluorescent light by exposure to the excitation light applied from the electromagnetic radiation emitting device 10. As the detecting device 14, any known image-taking device (light detecting device) such as a CCD cameral or a photodiode can be suitably used, provided that the device is adapted to detect the self-fluorescent light emitted from the marked contact lens 12 and convert the light signal of the self-fluorescent light into the electric signal. The image-taking device may be provided with a lens such as a microscope or a camera, for obtaining a significantly clear fluorescent image of the marked contact lens 12.

When the detecting device 14 is not arranged to detect only the light in the desired wavelength range, the detecting device 14 is preferably equipped with an optical filter or filters adapted to pass therethrough only the light in the desired wavelength range. The detecting device 14 with the optical filter(s) can selectively detect only the self-fluorescent light emitted from the marked contact lens 12, and does not pass therethrough a redundant light, i.e., the excitation light having a considerably higher degree of intensity than the self-fluorescent light emitted from the marked contact lens 12. Accordingly, the obtained fluorescent image of the marked contact lens 12 has a high degree of contrast.

Figure 2:
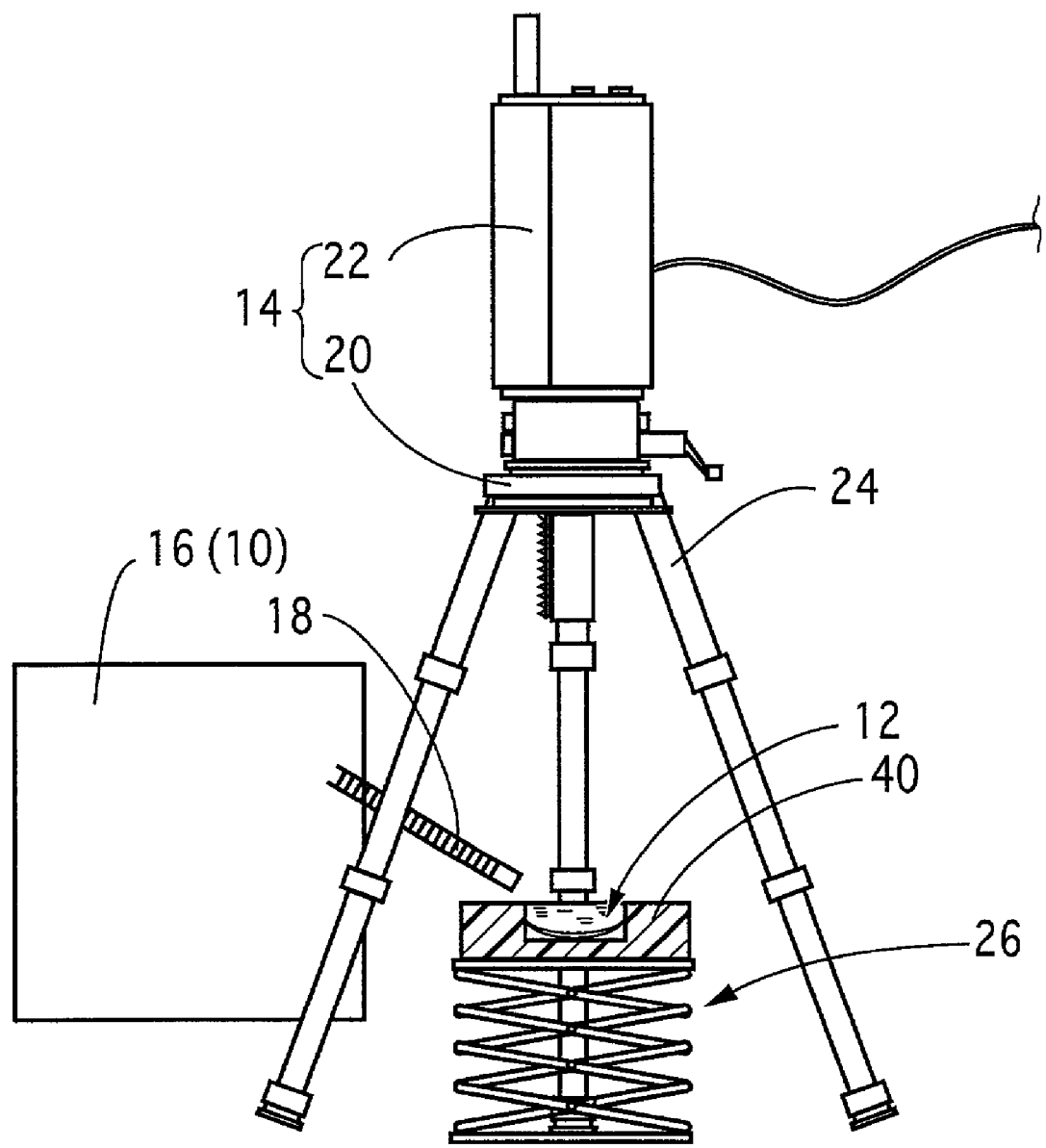
FIG. 2 is a view showing one example of an image taking system of the reading device.

One example of an image-taking system including the electromagnetic radiation emitting device 10 and the detecting device 14 for taking the fluorescent image of the marked contact lens 12 is shown in FIG. 2. In FIG. 2, the reference numeral 16 indicates a mercury-xenon lamp equipped with a band pass filter which passes a UV light whose wavelength is in a range of 330–380 nm. The mercury-xenon lamp 16 corresponds to the electromagnetic radiation emitting device 10 in FIG. 1. The UV light emitted from the mercury-xenon lamp 16 is applied through a UV light guide 18 toward the upper surface of the marked contact lens 12.

The self-fluorescent light emitted from the marked contact lens 12 is detected by the detecting device 14 which includes a camera lens 20 and a digital CCD camera 22 and which is equipped with a UV cut-off filter. In the present embodiment, the detecting device 14 is placed on a camera stand 24 and located above the marked contact lens 12, as shown in FIG. 2. The marked contact lens 12 is accommodated in a container 40 which will be described, and the container 40 is placed on a stage in the form of an elevator 26.

The fluorescent image of the marked contact lens 12 detected as described above is fed to an image data processing device 28 which is constituted by any suitable known microcomputer such as a personal computer. The image data processing device 28 includes a character reading portion 32 functioning as an optical character recognition (OCR) portion 30, a comparison portion 34 for comparing the obtained data with reference data, and a judging portion 36 for judging whether the obtained data are identical with the reference data.

Image data representative of the fluorescent image are first applied to the character reading portion 32 of the OCR portion 30 to read the identifying mark formed in the marked contact lens 12 such as characters or figures which represent the specifications of the lens (e.g., a base curve value, a diameter of the lens, etc.) and a production number of the lens. The character reading portion 32 utilizes a known character recognition function such as a pattern matching function or a neuro-learning function.

The character data which represent the information on the marked contact lens 12 read by the character reading portion 32 are applied to the comparison portion 34 where the obtained character data (obtained lens information) are compared with reference data (prepared lens information). For instance, the reference data are read from a bar code and a two-dimensional code given on a product label, an ID chip, a data storage medium such as FD, MO, CD-R(W), or a data base stored in a host computer. The comparison portion 32 reads suitable reference data depending upon the character data which are read by the character reading portion 32. When the identifying mark formed in the marked contact lens 12 represents an optical power value of the lens, a desired optical power value is read as the reference data.

The judging portion 36 judges whether the obtained character data are identical with the reference data. The result of the judgment is output to an output device 38 in the form of a display, a printer, a warning device, etc. The obtained character data and the result of the judgment may be stored in a an ID chip, a data storage medium such as FD, MO, CD-R(W), etc., or a data base in a host computer.

On the basis of the judgment made as described above, the ophthalmic lens which has character data different from the reference data is distinguished from the desired ophthalmic lens having the character data identical with the reference data. Accordingly, the present arrangement effectively avoids the conventionally experienced problem of delivering, to a user, improper lenses having specifications not suitable to the eye of the specific user. Further, the mass-produced ophthalmic lenses having different specifications are effectively distinguished from one another in the production line.

In the present method using the identifying mark reading device constructed as described above, the marked ophthalmic lens (marked contact lens 12) is uniformly irradiated with the predetermined excitation light over the entire surface thereof, and the self-fluorescent light emitted from the lens upon irradiation with the excitation light is detected to give the fluorescent image of the lens. The thus obtained fluorescent image of the lens has a higher degree of contrast than a directly photographed image of the lens, whereby the identifying mark is represented by the fluorescent image with a high degree of clarity. Therefore, the identifying mark formed in the ophthalmic lens can be easily recognized, so that the information of the marked ophthalmic lens can be advantageously obtained.

In the present method described above, the identifying mark clearly represented by the fluorescent image can be automatically read, for thereby permitting a speedy and continuous reading of the identifying mark formed in each of the mass-produced ophthalmic lenses, and significantly reducing the labor cost required for reading the identifying mark, so that the cost for manufacture of the ophthalmic lens can be effectively reduced.

The marked contact lens 12 is immersed in a liquid medium 42 such as a saline solution or a contact lens storing liquid. The liquid medium 42 is accommodated in the container 40 which has a cylindrical shape with a relatively small depth. The excitation light is applied to the marked contact lens 12 while the lens 12 is immersed in the liquid medium 42 accommodated in the container 40. The material of the container 40 is preferably selected from among those which do not emit a fluorescent light by exposure to the excitation light, for obtaining the fluorescent image of the lens 12 having a high degree of contrast. In view of this, it is preferable to employ, as the material of the container 40, a quartz glass or a any known metallic material such as stainless steel or aluminum. Those materials are not excited by the UV radiation having a wavelength of 200–400 nm. The material of the container 40 is not limited to those described above, but any other known materials which emit a fluorescent light by exposure to the excitation light may be used, as long as the fluorescent light emitted from the material of the container 40 does not prevent the reading or recognition of the identifying mark represented by the fluorescent image of the lens 12.

In addition, it is preferable that the liquid medium 42 in which the marked contact lens 12 is immersed does not emit a fluorescent light by exposure to the excitation light. If the marked contact lens 12 were stained, the identifying mark formed in the lens 12 would not be clearly recognized. In view of this, it is preferable that the identifying mark should be read while the lens 12 is kept clean.

While the present invention has been described in detail in its presently preferred first embodiment directed to the method of reading the identifying mark formed in the ophthalmic lens, it is to be understood that the invention is not limited to the details of the first embodiment.

In the illustrated first embodiment, the optical character recognition (OCR) portion 30 reads the characters as the identifying mark formed in the marked contact lens 12, so that the information on the marked contact lens 12 is obtained. In addition to the characters, other identifying marks such as figures, symbols, etc. can be read. For instance, code marks such as a bar code and two dimensional codes such as a veri code can be read by using a reading device adapted to read the code marks, for thereby obtaining coded information of the lens. Examples of the identifying mark or information are shown in the following TABLE 1.

Figure 3:
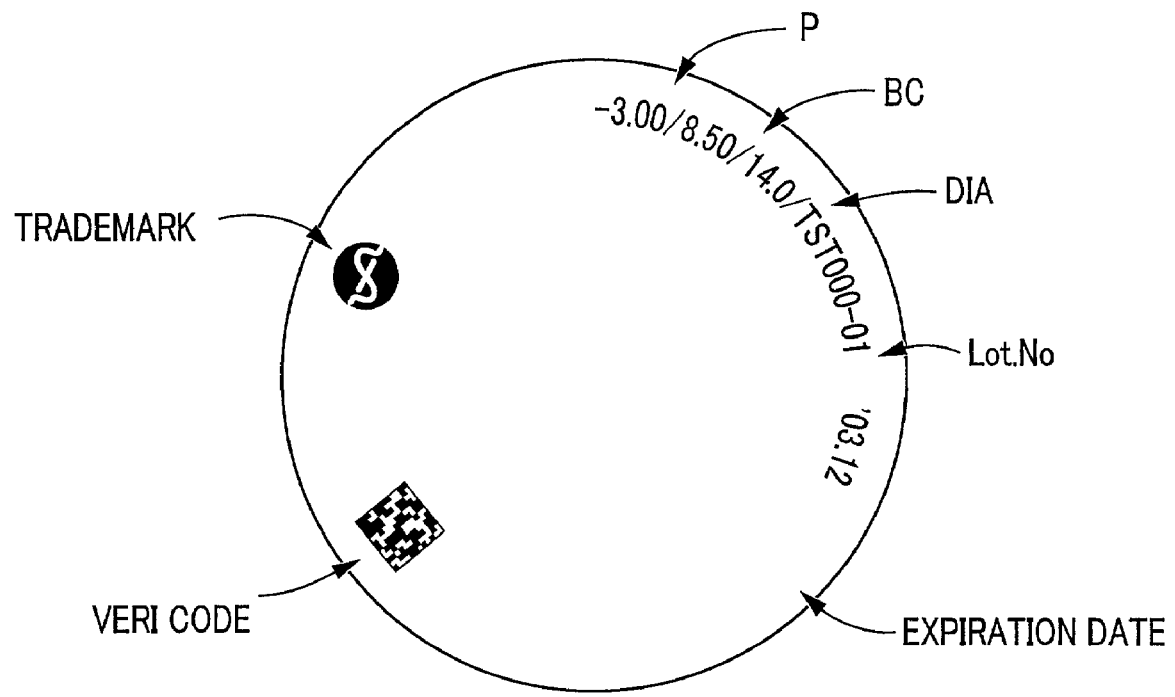
FIG. 3 is a schematic view showing a contact lens with the identifying marks, to which the present invention is applied.

It is noted that the identifying marks are not limited to those indicated in the TABLE 1. FIG. 3 schematically shows one example of the marked contact lens in which the identifying marks are formed.

TABLE 1

| Information on the ophthalmic lens | Examples of the identifying mark |
|---|---|
| Kind of the ophthalmic lens | MENICON Z, MENICON SUPER EX, MENICON SOFT MA (Product Name) |
| Base curve (BC) (radius of curvature at vertex) | 8.00 (mm) |
| Diameter (DIA) | 8.8 (mm) |
| Center thickness | 0.15 (mm) |
| Optical power (P)*[1] | 3.00 (diopter) |
| Manufacturing date or number | 2000.01.01 |
| Material | PMMA |
| Storing liquid | Saline solution |
| Expiration date | 2010.01.01 |
| Manufacturing Plant | Seki-Plant, Seki, Gifu-ken |
| Lot No. | DE0892272 |
| Two dimensional code | (two dimensional data of at least one of those described above) |

*[1]The monofocal contact lens has a single optical power value, while a multifocal contact lens such as a bifocal contact lens has a plurality of optical power values. In the toric contact lens, other information such as an astigmatic axis orientation and an additional power is given.

The optical filters such as the band pass filter and the cut-off filter may be disposed otherwise. For instance, the optical filters may be disposed outside the electromagnetic radiation emitting device 10 and the detecting device 14, respectively, provided that the optical filters are located between the excitation light source and the marked contact lens, and between the image-taking device and the marked contact lens. The optical filters are not essential, but may be suitably provided depending upon the excitation light source and the image-taking device.

The structure of the image data processing device 28 is not limited to that in the illustrated first embodiment, but may be suitably determined depending upon the forms of the identifying marks to be read.

In the illustrated first embodiment, the identifying mark is automatically read or recognized in the image data processing device 28. The identifying mark may be read manually by the worker from the output fluorescent image of the lens. In this case, for permitting the worker to easily recognize the identifying mark, it is preferable that the fluorescent image of the lens detected by the detecting device 14 is represented by a plurality of colors corresponding to respective values of luminance at local portions of the ophthalmic lens. Alternatively, it is preferable that the output device is arranged to provide an enlarged fluorescent image of the lens.

Figure 4:
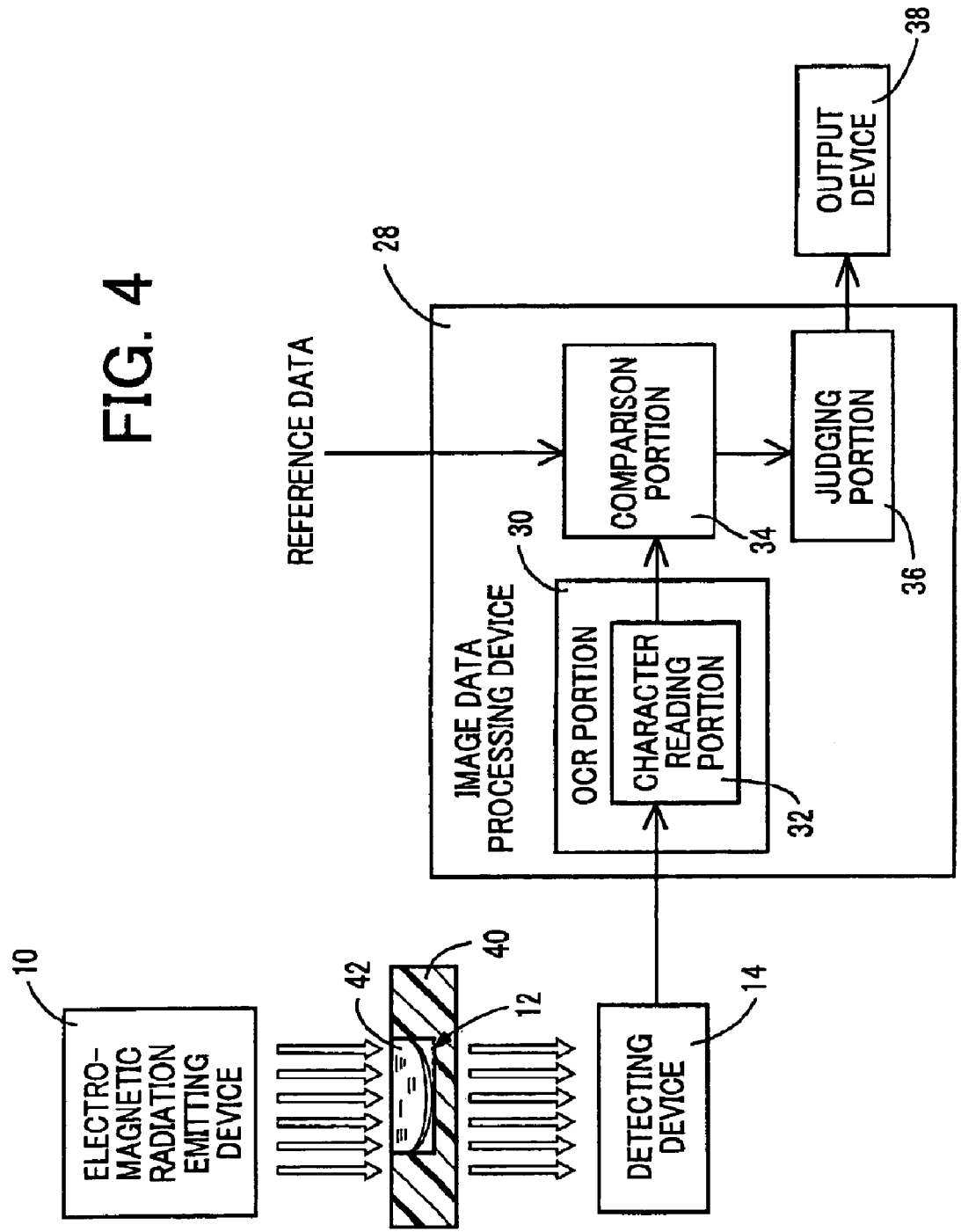
FIG. 4 is a schematic view showing another example of the reading device for reading the identifying mark formed in the ophthalmic lens.

In the illustrated first embodiment, the electromagnetic radiation emitting device 10 and the fluorescent image detecting device 14 are located above the marked contact lens 12, shown in FIG. 1, such that the excitation light was applied toward the upper surface of the marked contact lens 12, and such that the self-fluorescent light emitted from the marked contact lens 12 is detected on the upper side of the lens 12. The locations of the devices 10, 14 with respect to the marked contact lens 12 are not particularly limited, provided that the self-fluorescent light emitted from the lens 12 by exposure to the excitation light can be effectively detected. For instance, the excitation light may be applied from the device 10 toward the upper surface of the lens 12 while the device 14 located below the lens 12 may detect the self-fluorescent light on the lower side of the lens 12, as shown in FIG. 4. Further, the electromagnetic radiation emitting device 10 and the detecting device 14 may be located above the lens 12 with the container 40 being interposed therebetween.

In the illustrated first embodiment, the marked contact lens 12 is accommodated in the container 40 with its base curved surface facing upward. The marked contact lens 12 may be positioned with its front curved surface facing upward.

In the illustrated first embodiment, the identifying mark is read with the marked contact lens 12 being immersed in a predetermined amount of the liquid medium 42 accommodated in the container 40. The structure of the container 40 is not limited to that in the illustrated embodiment. Further, the container 40 and the liquid medium 42 are not essential.

Figure 5:
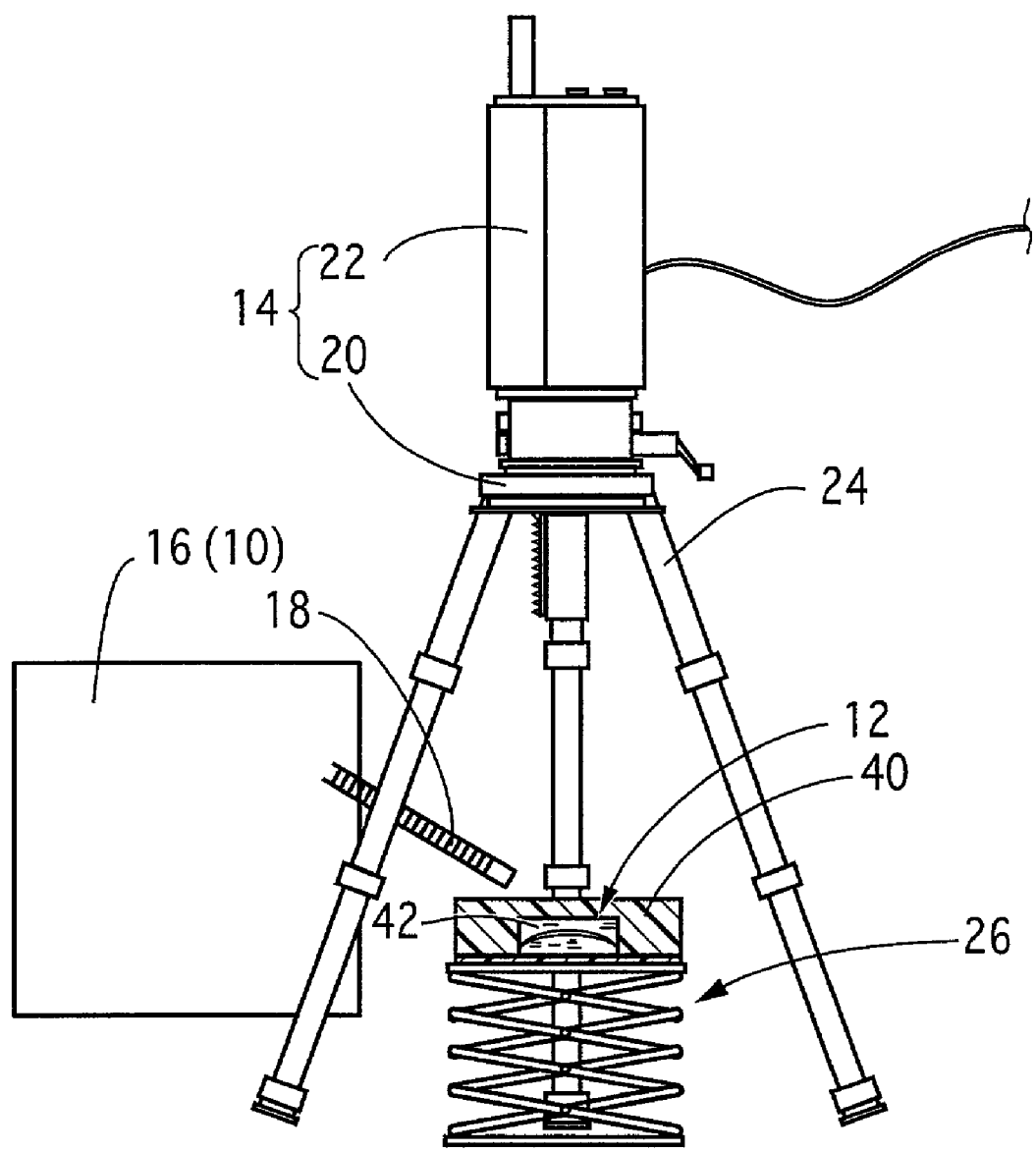
FIG. 5 is a schematic view showing another example of the image taking device of the reading device.

In the illustrated first embodiment, the identifying mark is read while the container 40 in which the marked contact lens 12 is accommodated is placed on the elevator 38, as shown in FIGS. 2 and 5. In place of the elevator 38, a known transferring device such as a belt conveyor may be used, for thereby permitting a continuous reading of the identifying marks formed in each of a plurality of marked contact lenses.

Referring next to FIGS. 8–11, there will be explained a second and a third embodiment of the present invention, which are directed to a method of obtaining a thickness of an ophthalmic lens, as another example of the particulars which give information on the ophthalmic lens. In these second and third embodiments, the same reference numerals as used in the above-described first embodiment of FIGS. 1–7 are used to identify the corresponding components, and a detailed description of which is dispensed with.

Figure 8:
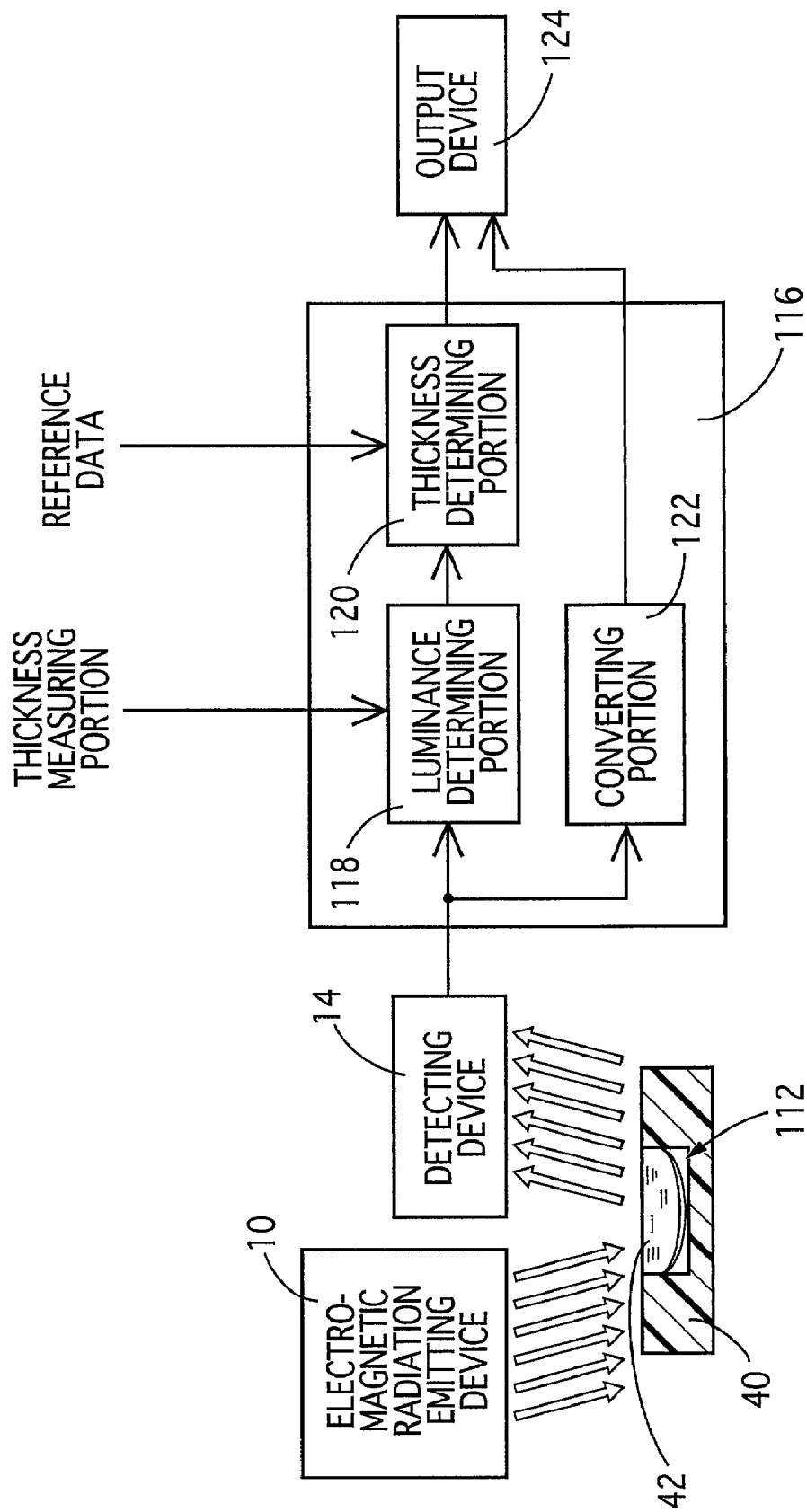
FIG. 8 is a schematic view showing one example of a thickness measuring device for measuring a thickness of the ophthalmic lens, which device is constructed according to the invention.

FIG. 8 schematically shows a thickness measuring device, which is constructed according to the second embodiment, for measuring the thickness of an ophthalmic lens. The thickness measuring device of FIG. 8 includes the electromagnetic radiation emitting device 10, the fluorescent image detecting device 14 (which are the same as those explained in the above-described first embodiment), a computer 116, and an output device 124. The wavelength of the excitation light for irradiating the ophthalmic lens in the form of a contact lens 112 and the wavelength of the self-fluorescent light emitted from the contact lens 112 are within the respective preferred ranges described above with respect to the first embodiment. In this second embodiment, too, a suitable optical filter may be interposed between the device 10 and the contact lens 112 for the purpose of effectively irradiating the contact lens 112 with the desired excitation light. As in the above-described first embodiment, the detecting device 14 for detecting the fluorescent image of the contact lens 112 is preferably equipped with a suitable optical filter or filters for the purpose of obtaining the fluorescent image of the contact lens 112 with a high degree of contrast. The structure of the image-taking system including the electromagnetic radiation emitting device 10 and the fluorescent image detecting device 14 is similar to that shown in FIG. 2 described above with respect to the first embodiment, and a detailed description of which is dispensed with.

The fluorescent image of the contact lens 112 detected by the detecting device 14 is fed to the computer 116 which includes a luminance determining portion 118 for determining a luminance value at a predetermined thickness measuring portion, a thickness determining portion 120 for determining the thickness at the thickness measuring portion on the basis of the luminance value determined by the luminance determining portion 118, and a converting portion 122 for converting the detected fluorescent image of the contact lens 112 into a color image. The computer 116 is constituted by any known microcomputer such as a personal computer.

More specifically described, image data representative of the fluorescent image are applied to the luminance determining portion 118 and the converting portion 122, respectively. The detected fluorescent image of the contact lens 112 represents a distribution of respective luminance values of local portions of the contact lens 112. The luminance determining portion 118 first determines a position of the predetermined thickness measuring portion of the lens in the fluorescent image, on the basis of suitably input data (e.g., numerical values) indicative of the position of the thickness measuring portion, and then obtains the luminance value at the thickness measuring portion on the basis of the distribution.

The thickness determining portion 120 determines the thickness of the thickness measuring portion on the basis of the obtained luminance value and according to reference data in the form of a predetermined relationship between the thickness of the thickness measuring portion and the luminance value of the self-fluorescent light generated by irradiation with the excitation light. One example of the reference data is a calibration curve which is obtained based on a finding that there is a predetermined correlation between the thickness of the ophthalmic lens and the luminance of the self-fluorescent light emitted from the material of the ophthalmic lens. The calibration curve is obtained in the following manner, for instance. Initially, there are prepared a plurality of plates which are formed of the same material as the ophthalmic lens and which have mutually different thickness values. The luminance values are determined for each of the different plates in a manner similar to that in detecting the fluorescent image of the contact lens 112 described above. The determined luminance values are plotted in relation to the respective thickness values, for thereby providing the calibration curve indicating the predetermined relationship between the thickness of the ophthalmic lens and the luminance of the self-fluorescent light emitted from the ophthalmic lens. The thickness of the thickness measuring portion is determined on the basis of the luminance value determined by the luminance determining portion 18 and according to the reference data (predetermined relationship) obtained as described above. Since the reference data are used every time when the thickness of the ophthalmic lens is measured, the reference data are preferably stored in a magnetic disk such as a hard disk or a floppy disk, or a known data storage medium such as a magneto-optical disk, a photo disk, or an IC card.

The thickness of the thickness measuring portion determined as described above is output to the output device 124 such as a display device and a printer, so that the worker can recognize the thickness of the thickness measuring portion of the contact lens 112.

The fluorescent image of the contact lens 112 applied to the converting portion 122 is represented by a distribution of a plurality of different colors or color gradation values corresponding to respective values of luminance of infinitesimal local portions or pixel areas of the contact lens 112. The output device 124 outputs the fluorescent image of the contact lens 112 represented by the distribution of different colors, whereby the worker can easily recognize the distribution of the luminance values of the contact lens 112. The present second embodiment may be modified such that the thickness of any desired portion of the contact lens 112 can be quickly recognized according to a prepared relationship among the thickness of the ophthalmic lens, the luminance of the self-fluorescent light, and the color gradation value.

According to the present embodiment, the ophthalmic lens is uniformly irradiated with the predetermined excitation light over the entire surface thereof, and the fluorescent image of the lens which represents the distribution of the luminance values of the local portions of the lens is detected while the lens is emitting the self-fluorescent light. The thickness of the predetermined thickness measuring portion can be obtained on the basis of the distribution. Accordingly, the thickness of the ophthalmic lens can be easily obtained in a non-contact manner, namely, without using any members in contact with the ophthalmic lens, for thereby effectively avoiding the conventionally experienced risk of damaging the lens surface. Further, the present method permits an accurate measurement of the thickness, e.g., the optical center thickness, of various ophthalmic lenses such as a mono-focal lens which has the smallest thickness at its geometrical center, a toric and a bifocal lens which have a thin-walled portion at its lower or upper portion, and other lenses whose optical center is offset from its geometrical center. Unlike the conventional thickness measuring method using the ultrasonic wave, the present method significantly reduces a required time for measuring the thickness of the ophthalmic lens.

In the present method, the self-fluorescent light is detected over the entire surface of the ophthalmic lens, rather than in a predetermined limited portion of the lens. Accordingly, the position of the desired thickness measuring portion can be easily and accurately determined in the fluorescent image. In addition, not only the center thickness, but also the thickness at any desired portion of the ophthalmic lens can be obtained in a single measuring operation.

Since the fluorescent image of the ophthalmic lens is represented by a plurality of different colors corresponding to the respective luminance values of local portions of the lens, the thickness of the lens or the distribution of the luminance values of the ophthalmic lens can be easily recognized.

Figure 9:
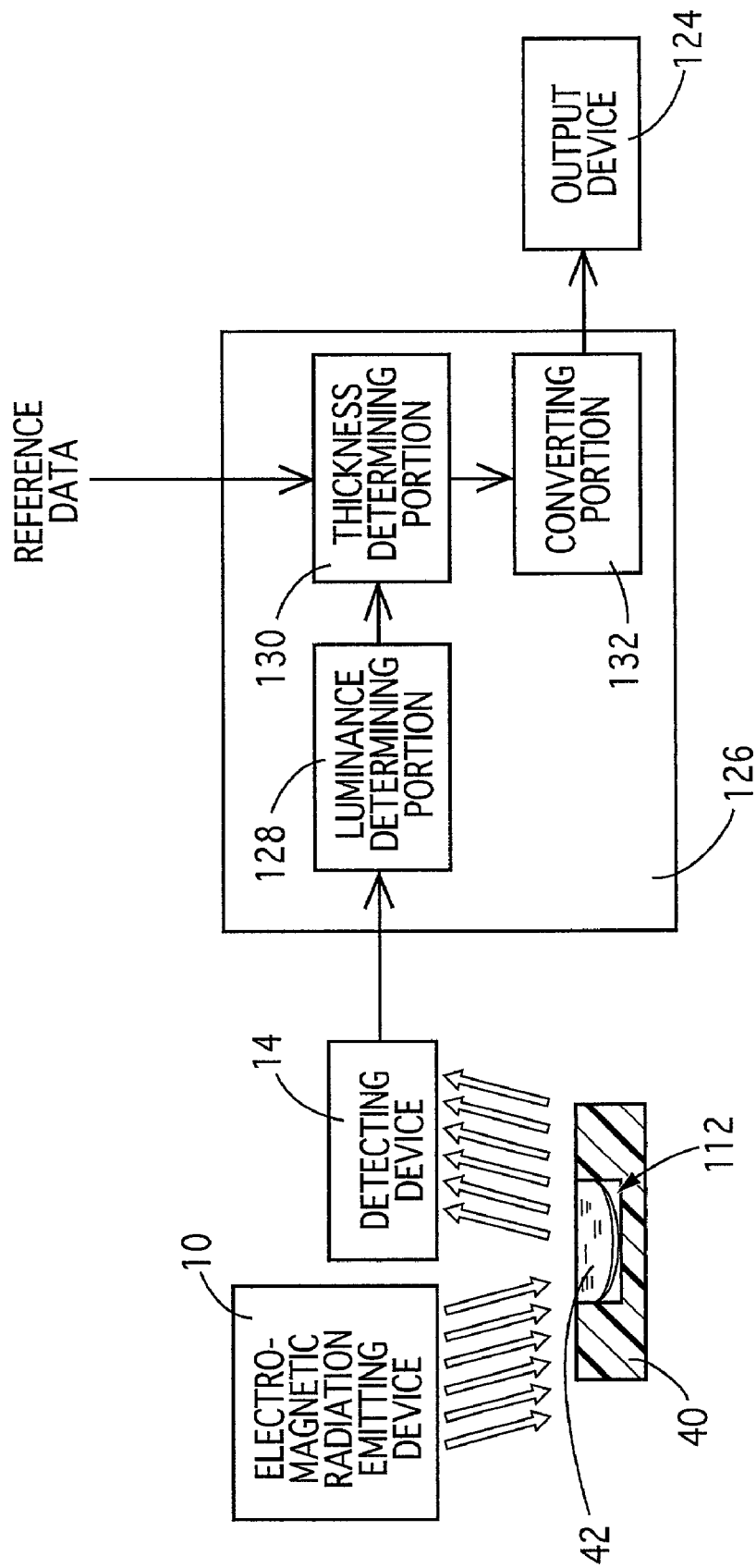
FIG. 9 is a schematic view showing another example of the thickness measuring device.

The structure of the thickness measuring device is not limited to that in the illustrated second embodiment, but may be modified as shown in FIG. 9, for instance. In FIG. 9, the same reference numerals as used in FIG. 8 are used to identify the corresponding components, which will not be described below to avoid redundant description.

The thickness measuring device of FIG. 9 constructed according to the third embodiment of the invention has a computer 126 which is different from the computer 116 of the thickness measuring device of FIG. 8. The computer 126 of the thickness measuring device according to this third embodiment includes a luminance determining portion 128, a thickness determining portion 130, and a converting portion 132. Like the computer 116 of FIG. 8, the computer 126 of FIG. 9 is constituted by any known microcomputer such as a personal computer.

More specifically described, image data representative of the fluorescent image of the contact lens 112 detected by the detecting device 14 are initially applied to the luminance determining portion 128. The fluorescent image represents a distribution of respective luminance values of the infinitesimal local portions or pixel areas of the contact lens 112. The luminance determining portion 128 determines the respective luminance values of the local portions of the contact lens 112 on the basis of the distribution.

The obtained luminance values of the local portions of the contact lens 112 are applied to the thickness determining portion 130, and the thickness values corresponding to the obtained luminance values of the local portions of the contact lens 112 are determined according to the prepared reference data described above.

The thickness values determined for the local portions of the contact lens 112 are applied to the converting portion 132. In the converting portion 132, the distribution of the thickness values of the contact lens 112 is represented by a plurality of different colors or color gradation values corresponding to the respective thickness values, and accordingly the luminance values, of the infinitesimal local portions of the contact lens 112. The output device 124 outputs the fluorescent image of the contact lens 112 represented by the distribution of different colors, whereby the worker can easily obtain the thickness at any desired portion of the contact lens 112.

The thickness measurement of the contact lens 112 is conducted while the lens 112 is accommodated in the container 40 shown in FIGS. 8 and 9. As in the illustrated first embodiment of FIGS. 1–7, the material of the container 40 is not particularly limited, but is preferably selected from among those which do not emit a fluorescent light by exposure to the excitation light, for obtaining the thickness of the contact lens 112 with high accuracy. It is preferable to use, as the material of the container 40, a quartz glass or any known metallic material such as stainless steel or aluminum. Those materials are not excited by the IN radiation having a wavelength of 200–400 nm. When the container 40 is formed of a material which emits a fluorescent light by exposure to the excitation light, the luminance values of the fluorescent image of the contact lens 112 need to be determined by taking account of the luminance of the fluorescent light emitted from the material of the container, or the container formed of the material which emits the fluorescent light needs to be used for obtaining the reference data.

In addition, it is preferable that the liquid medium 42 in which the contact lens 112 is immersed does not emit a fluorescent light by exposure to the excitation light. If the contact lens 112 and the container 40 were stained, it would be difficult to accurately obtain the thickness of the contact lens 112. In view of this, it is preferable that the thickness measurement is conducted with the lens being kept clean, at a suitable timing such as during its manufacture or prior to its shipment.

While the present invention has been described in detail in its presently preferred second and third embodiments directed to the method of obtaining the thickness of the ophthalmic lens, it is to be understood that the invention is not limited to the details of the second and third embodiments. The present method of obtaining the thickness of the ophthalmic lens may be practiced by using a thickness measuring device different from those shown in FIGS. 8 and 9.

In the illustrated second and third embodiments, the luminance values in the fluorescent image of the ophthalmic lens are obtained for the infinitesimal local portions or pixel areas. The luminance values may be obtained for a desired area of the thickness measuring portion, which has various shapes such as a circle (having a diameter of 1 μm, for instance), a cross, a rectangle, a square, a polygonal, etc. In obtaining the thickness of the thickness measuring portion which is composed of a plurality of pixels, the luminance values of the respective pixels are preferably averaged, and the average value of luminance is used to determine the thickness of the thickness measuring portion, for an improved measuring accuracy. The thickness measuring portion may be determined otherwise, for instance, by pointing a desired portion of the fluorescent image of the lens indicated on the monitor.

In addition to the thickness at a predetermined portion of the ophthalmic lens, the smallest or the largest thickness of the ophthalmic lens and the positions in the lens which give the largest and small thickness, respectively, can be obtained from the intensity (luminance) of the detected self-fluorescent light.

In the illustrated second and third embodiments, the converting portions 122, 132 are arranged such that the fluorescent image of the ophthalmic lens detected by the detecting device 14 is represented by a plurality of colors or color gradation values corresponding to the respective luminance values of local portions of the lens, whereby the color image of the lens is output to the output device 124. The converting portion 122, 132 is not an essential component in the present invention.

The optical filters such as the band pass filter and the cut-off filter may be disposed otherwise. For instance, the optical filters may be disposed outside the electromagnetic radiation emitting device 10 and the detecting device 14, respectively, provided that the optical filters are located between the excitation light source and the ophthalmic lens, and between the image-taking device and the ophthalmic lens. The optical filters are not essential, but may be suitably provided depending upon the excitation light source and the image-taking device. If the excitation light source is arranged to emit only a light in the desired wavelength range, the optical filters need not be provided.

The structures of the computers 116, 126 are not limited to those described above. For instance, the thickness of the thickness measuring portion may not be determined by the computers 116, 126, but may be determined by the worker on the basis of the obtained luminance and according to the calibration curve, for instance.

In the illustrated second and third embodiments, the entire surface of the ophthalmic lens is irradiated with the excitation light, and the fluorescent image of the ophthalmic lens is detected. Only a desired thickness measuring portion may be irradiated with the excitation light for detecting the self-fluorescent light only from the desired thickness measuring portion.

In the illustrated second and third embodiments, the electromagnetic radiation emitting device 10 and the detecting device 14 are located above the ophthalmic lens (112). The electromagnetic radiation emitting device 10 and the detecting device 14 may be located in opposed relation to each other with the ophthalmic lens being interposed therebetween.

In measuring the thickness of the contact lens (112), the contact lens 112 may be accommodated in the container 40 with its base curved surface facing upward, as shown in FIGS. 8 and 9, or the contact lens 112 may be positioned with its front curved surface facing upward.

In the illustrated second and third embodiments, the principle of the present invention is applied to the toric lens and the bifocal lens. The principle of the present invention is applicable to contact lenses and intraocular lenses having various configurations and formed of various materials.

Referring next to FIGS. 12–16, there will be described a fourth embodiment of the present invention which is directed to a method of detecting an angular position of an ophthalmic lens, as another example of the particulars which give information on the ophthalmic lens. The angular position is defined, for instance, by a position of one of the thickest circumferential portion, a distant vision correction region, and a near vision correction region of the ophthalmic lens, in its circumferential direction. In this fourth embodiment, the same reference numerals as used in the above-described first embodiment of FIGS. 1–7 are used to identify the corresponding components, and a detailed description of which is dispensed with.

Figure 12:
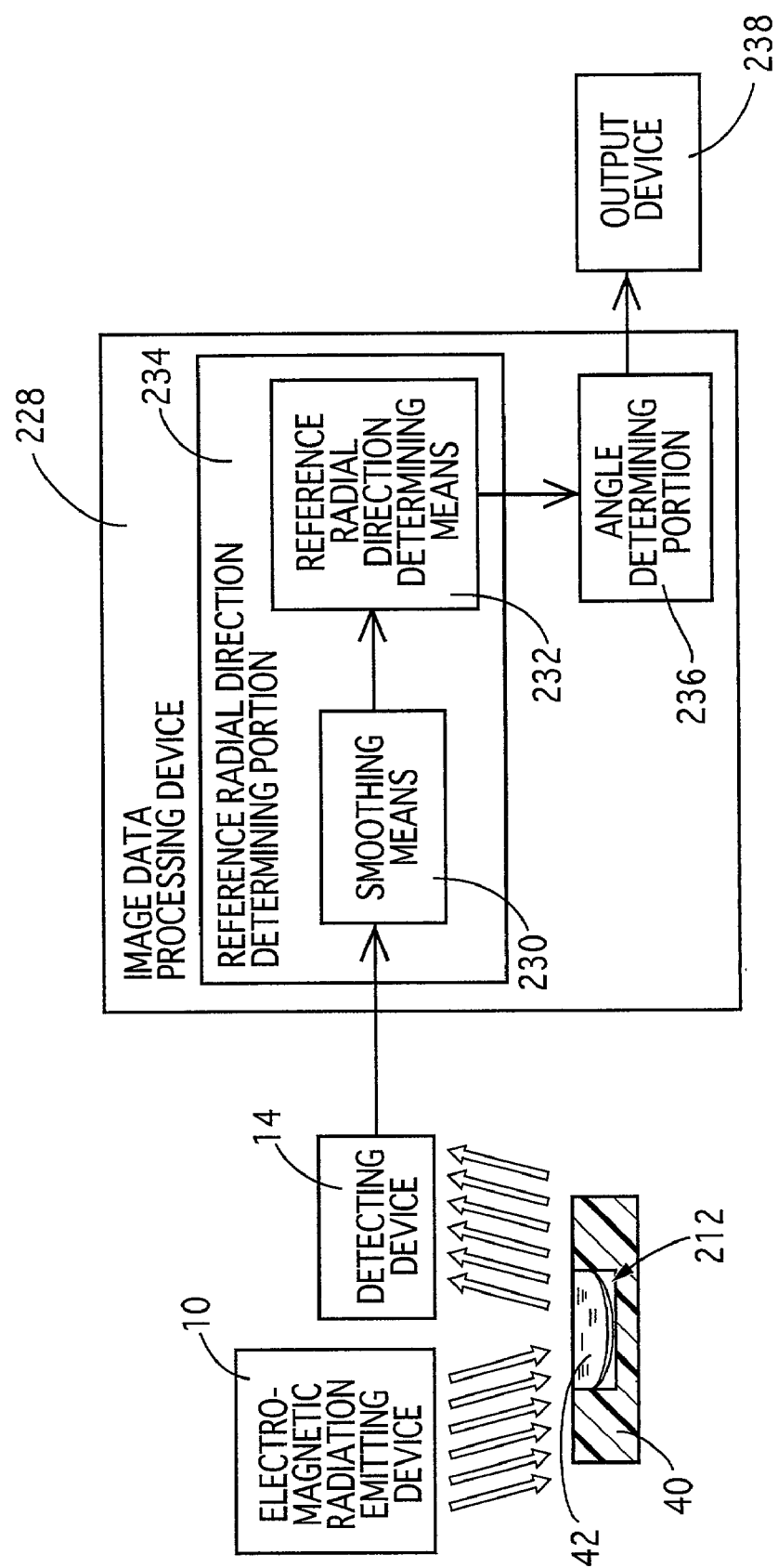
FIG. 12 is a schematic view showing one example of an angular position detecting device for detecting an angular position of the ophthalmic lens, which device is constructed according to the invention.

FIG. 12 schematically shows an angular position detecting device, which is constructed according to the fourth embodiment, for detecting the angular position of an ophthalmic lens. The angular position detecting device of FIG. 12 includes the electromagnetic radiation emitting device 10, the fluorescent image detecting device 14 (which are the same as those explained in the above-described first embodiment), an image data processing device 228, and an output device 238. The wavelength of the excitation light for irradiating the ophthalmic lens in the form of a contact lens 212 and the wavelength of the self-fluorescent light emitted from the contact lens 212 are within the respective preferred ranges described above with respect to the first embodiment. In this fourth embodiment, too, a suitable optical filter may be interposed between the device 10 and the contact lens 222 for the purpose of effectively irradiating the contact lens 212 with the desired excitation light. As in the above-described first embodiment, the detecting device 14 for detecting the fluorescent image of the contact lens 212 is preferably equipped with a suitable optical filter or filters for the purpose of obtaining the fluorescent image of the contact lens 212 with a high degree of contrast. The structure of the image-taking system including the electromagnetic radiation emitting device 10 and the fluorescent image detecting device 14 is similar to that shown in FIG. 2, and a detailed description of which is dispensed with.

Image data representative of the fluorescent image detected by the detecting device 14 may be directly output to the output device 238. In the present embodiment, however, the image data representative of the fluorescent image are applied to the image data processing device 228. The fluorescent image represents a distribution of respective luminance values of local portions of the contact lens 212. The image data processing device 228 includes a reference radial direction determining portion 234 which comprises a smoothing means 230 for smoothing the luminance values of the local portions of the fluorescent image and a reference radial direction determining means 232 for determining a reference radial direction, and an angle calculating portion 236 for calculating an angle defined by the reference radial direction and a horizontal axis L of the fluorescent image of the contact lens 212. The reference radial direction is defined by the geometrical center of the lens and the thickest circumferential portion of the lens. The thickest circumferential portion of the lens is aligned with the reference radial direction. The image data processing device 228 is constituted by any known microcomputer such as a personal computer.

Figure 13:
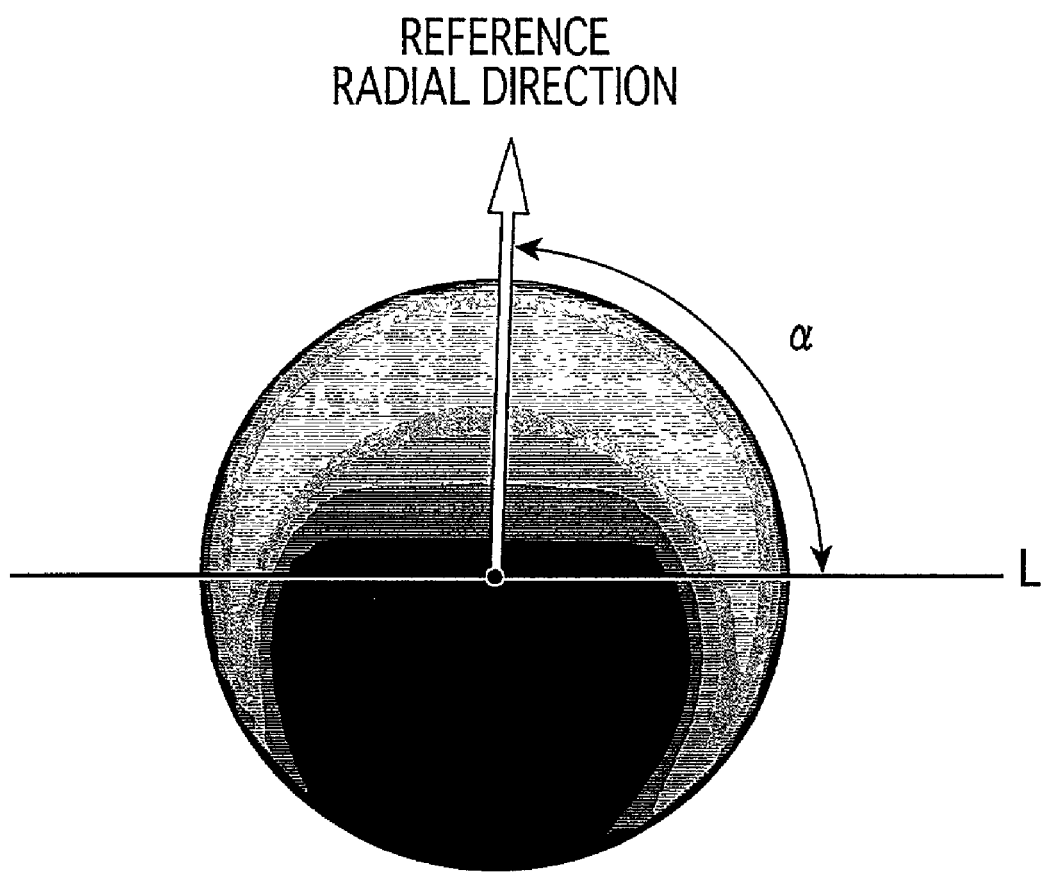
FIG. 13 is a schematic view showing a fluorescent image of the ophthalmic lens, which indicates the reference radial direction and the angle between the reference radial direction and the horizontal axis of the lens.

The image data representative of the fluorescent image of the contact lens 212 are initially applied to the smoothing means 230, so that the fluorescent image of the contact lens 212 is subjected to a smoothing treatment. Described in detail, the luminance values at the local portions of the lens 212, especially at the portions having relatively high luminance values, are smoothed for the purpose of averaging the luminance values at those portions to minimize variations in the luminance values, whereby the distribution of the luminance values in the fluorescent image of the contact lens 212 can be clearly recognized. FIG. 13 schematically shows the smoothed fluorescent image of the contact lens 212.

The smoothed fluorescent image of the contact lens 212 is applied to the reference radial direction determining means 232 to determine, as the reference radial direction, a radial direction extending from the geometric center of the lens toward a circumferential position of the lens exhibiting high luminance values, as shown in FIG. 3.

The determined reference radial direction is applied to the angle calculating portion 236 to calculate an angle a defined by the reference radial direction and the horizontal axis L of the fluorescent image of the contact lens 212.

The calculated angle a is output to the output device 238 such as a known display device or a printer, so that the worker can recognize the reference radial direction. According to the present embodiment, the angular position of the contact lens 212 defined by the reference radial direction which extends from the geometrical center of the lens toward the thickest circumferential portion of the lens can be accurately detected, whereby various characteristic inspections of the contact lenses 212 can be conducted with high accuracy. In the astigmatism correction contact lens, a spherical power, a cylindrical power, an orientation of an astigmatic axis, and an amount of prism are accurately detected based on the determined angular position. The presbyopia correction contact lens is examined for its circumferential positions of the distant and near vision correction regions based on the determined angular position.

The present method permits detection of the angular position of a special contact lens which has circumferential portions having respective different thickness values and whose fluorescent image has a distribution of the luminance values shown in FIG. 3, for instance. Examples of the special contact lens include an astigmatism correction contact lens whose typical example is a toric lens, and a presbyopia correction contact lens whose typical example is a multifocal lens providing near and distant vision correction powers. It is noted that the present method is applicable to any other ophthalmic lenses which have circumferential portions having respective different thickness values by provision of the prism ballast mechanism, for example.

In the present method of detecting the angular position of the ophthalmic lens, the entire surface of the ophthalmic lens is irradiated with a suitable excitation light, and the fluorescent image of the lens is detected while the lens is emitting the self-fluorescent light by exposure to the excitation light. On the basis of the fluorescent image which represents the distribution of the luminance values on the surface of the ophthalmic lens, the reference radial direction and the angle a are determined, for thereby permitting an accurate detection of the angular position of the ophthalmic lens.

The present method permits an automatic and continuous detection of the angular position of each of a plurality of ophthalmic lenses, for thereby considerably reducing a time and a labor cost required for detecting the angular position of the ophthalmic lens.

In the present method wherein the self-fluorescent light emitted from the ophthalmic lens itself is detected, the fluorescent image of the ophthalmic lens is considerably clear, as compared with an image of an ophthalmic lens which is obtained by irradiating the lens with a visible light, and detecting a portion of the light which is reflected by the lens or which is not absorbed by the lens. Accordingly, unlike the conventional method, the present method permits an accurate detection or determination of the angular position of the lens (e.g., the reference radial direction).

As in the above-described first embodiment of FIGS. 1–7, the angular position of the contact lens 212 is detected with the lens 212 being immersed in the liquid medium 42 such as a saline solution, distilled water or a suitable contact lens storing liquid, as shown in FIG. 12. The liquid medium 42 is accommodated in the container 40 which has a cylindrical shape with a relatively small depth. The excitation light is applied to the contact lens 212 while the contact lens 212 is immersed in the liquid medium 42 accommodated in the container 40. As in the illustrated first embodiment, the material of the container 40 is not particularly limited, but is preferably selected from among those which do not emit a fluorescent light by exposure to the excitation light, for detecting the angular position of the ophthalmic lens with high accuracy. It is preferable to use, as the material of the container 40, a quartz glass or any known metallic material such as stainless steel or aluminum. Those materials are not excited by the UV radiation having a wavelength of 200–400 nm. The material of the container 40 is not limited to those described above, but any other known materials which emit a fluorescent light by exposure to the excitation light may be used, as long as the angular position can be effectively detected from the fluorescent image representing the distribution of the luminance values on the surface of the ophthalmic lens, without being adversely influenced by the fluorescent light emitted from the material of the container.

In addition, it is preferable that the liquid medium 42 in which the contact lens 212 is immersed does not emit a fluorescent light by exposure to the excitation light. If the contact lens 212 and the container 40 were stained, it would be difficult to accurately detect the angular position of the contact lens 212. In view of this, it is preferable that the detection of the angular position of the contact lens 212 is conducted with the contact lens 212 being kept clean, at a suitable timing such as during its manufacture or prior to its shipment.

Preferably, the contact lens 212 is accommodated in the container 40 such that the contact lens 212 is prevented from rotating therein, for the subsequent various inspections on the lens.

While the present invention has been described in detail in its presently preferred fourth embodiment directed to the method of detecting the angular position of the ophthalmic lens, it is to be understood that the invention is not limited to the details of the fourth embodiment.

In the illustrated fourth embodiment, the reference radial direction and the angle a which is defined by the reference radial direction and the horizontal axis L of the special contact lens are detected. On the basis of the obtained distribution of the luminance values on the surface of the ophthalmic lens and the obtained angular position of the lens, it is possible to detect, in the special contact lens, the respective circumferential positions of the near vision correction region and the distant vision correction region. Further, it is possible, in the presbyopia correction contact lens, to detect respective circumferential positions of two optical portions, and to determine that one and the other of the two optical portions are assigned to the corresponding one and the other of the near vision correction region and the distant vision correction region.

The optical filters such as the band pass filter and the cut-off filter may be disposed otherwise. For instance, the optical filters may be disposed outside the electromagnetic radiation emitting device 10 and the detecting device 14, respectively, provided that the optical filters are located between the excitation light source and the ophthalmic lens, and between the image-taking device and the ophthalmic lens. The optical filters are not essential, but may be suitably provided depending upon the excitation light source and the image-taking device.

The structure of the image data processing device 228 is not limited to that of the illustrated fourth embodiment, but may be suitably modified depending upon the angular position to be detected, e.g., the reference radial direction and the angle α, and the circumferential positions of the near and distant vision correction regions.

While the angular position of the ophthalmic lens such as the reference radial direction is detected by the image data processing device 228 in the illustrated fourth embodiment, the angular position may be detected by a manual operation of the worker on the basis of the output distribution of the luminance values represented by the fluorescent image of the ophthalmic lens. In this case, the fluorescent image is preferably represented by a plurality of colors or color gradation values corresponding to the respective values of the local portions of the ophthalmic lens, for easier recognition of the distribution of the luminance values.

Figure 14:
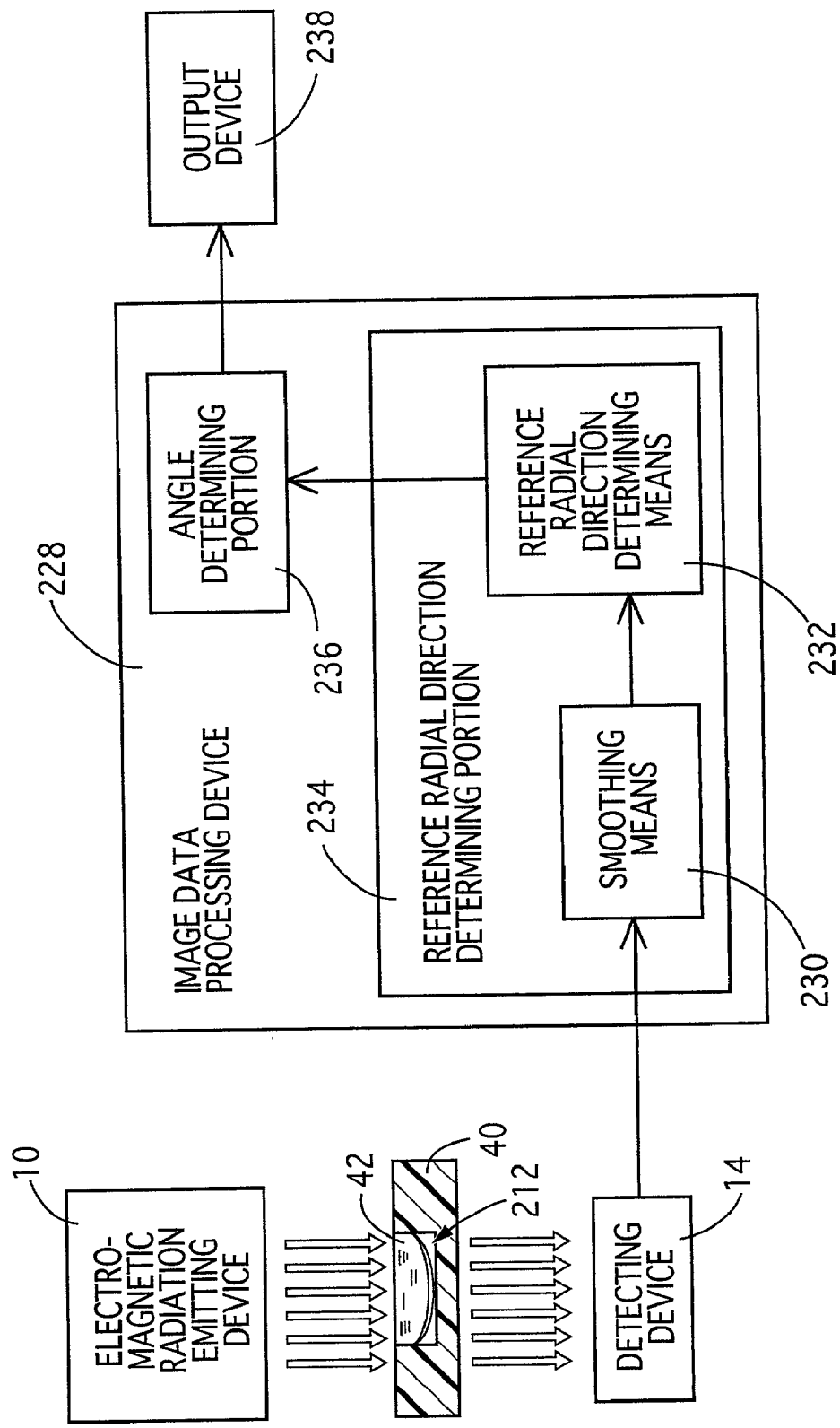
FIG. 14 is another example of the angular position detecting device.

In the illustrated fourth embodiment, the electromagnetic radiation emitting device 10 and the detecting device 14 are located above the contact lens 212, shown in FIG. 12, such that the excitation light was applied toward the upper surface of the contact lens 212, and such that the self-fluorescent light emitted from the contact lens 212 is detected on the upper side of the lens. The locations of the devices 10, 14 with respect to the contact lens 212 are not particularly limited, provided that the self-fluorescent light emitted from the contact lens 212 by exposure to the excitation light can be effectively detected. For instance, the excitation light may be applied from the device 10 toward the upper surface of the contact lens 212 while the device 14 located below the contact lens 212 may detect the self-fluorescent light on the lower side of the contact lens 212, as shown in FIG. 14. Alternatively, the electromagnetic radiation emitting device 10 may be located below the contact lens 212 while the detecting device 14 may be located above the contact lens 212.

In the illustrated fourth embodiment, the contact lens 212 is accommodated in the container 40 with its base curved surface facing upward. The contact lens 212 may be positioned with its front curved surface facing upward.

In the illustrated fourth embodiment, the angular position of the contact lens 212 is detected while the contact lens 212 is immersed in a predetermined amount of the liquid medium 42 accommodated in the container 40. The structure of the container 40 is not limited to that in the illustrated embodiment. Further, the container 40 and the liquid medium 42 are not essential.

In the illustrated fourth embodiment, the angular position of the contact lens 212 is detected while the container 40 in which the contact lens 212 is accommodated is placed on the elevator 38, as shown in FIG. 2. In place of the elevator 38, a known transferring device such as a belt conveyor may be used, for thereby permitting a continuous detection of the angular position of each of a plurality of contact lenses.

EXAMPLES

There will be described some examples of the present invention to further clarify the present invention. However, it is to be understood that the present invention is not limited to the details of the following examples and the presently preferred embodiments described above, but may be embodied with various changes, modifications and improvements, which may occur to those skilled in the art, without departing from the spirit of the present invention.

Example 1

Initially, there is prepared, as a sample lens, a new highly water-swollen soft contact lens in which an identifying mark "−3.00" which represents the optical power of the lens is engraved with a laser radiation. This sample contact lens has a base curve value of 8.50 mm and a diameter of 14.0 mm. By using an identifying mark reading device described below, the identifying mark formed in the sample lens was read in the following manner. As the reference data which are compared with the data to be obtained from the fluorescent image of the sample lens, "−3.00" is used.

-Reading device-
ORCA AQUACOSMOS package available from "KABUSHIKI KAISHA HAMAMATSU PHOTONICS, Japan
    image-taking device: digital CCD camera (C-4742-95-12NR)
                              F mount lens (f = 55 mm, F2.8S)
    image analyzing device: image data processing device (C7746-43E)
    image analyzing software: AQUACOSMOS BASIC SOFTWARE
                              (U 7501)
                              OCR SOFTWARE (self-made program
                              available from Menicon Co., Ltd., Japan)
Excitation light source: mercury-xenon lamp 200 W
Optical filter:
    <excitation light source>
        330–380 UV excitation filter
    <image-taking device>
        sky light filter
           (cut-off filter adapted to inhibit transmission of a light
           whose wavelength is not larger than 390 nm) and
        400 absorption filter
           (cut-off filter adapted to inhibit transmission of a light
           whose wavelength is not larger than 400 nm)

The sample contact lens was immersed in a predetermined amount of a saline solution accommodated in a blister case (40) with its base curved surface facing upward, as shown in FIG. 2. The blister case (40) accommodating the sample contact lens therein was placed on a stage of the detecting device (14) constituted by the digital CCD camera (22) equipped with the F mount lens (20).

The excitation light was applied toward the upper surface of the sample contact lens, and the self-fluorescent light emitted from the lens by the exposure to the excitation light was detected on the upper side of the lens. As the electromagnetic radiation emitting device (10), a mercury-xenon lamp (200 W) was used. This mercury-xenon lamp is equipped with a 330–380 UV excitation filter which permits transmission of a light having a wavelength in the neighborhood of 330–380 nm and whose spectral transmittance in the neighborhood of 340–390 nm is not less than 60%. The detecting device (14) is equipped with a sky light filter which inhibits transmission of a light whose wavelength is smaller than 390 nm and whose spectral transmittance at a wavelength of not less than 400 nm is not less than 80%. The detecting device (14) is also equipped with a 400 absorption filter which inhibits transmission of a light whose wavelength is smaller than 400 nm and whose spectral transmittance at a wavelength of not less than 420 nm is not less than 80%.

The image data representative of the fluorescent image taken by the detecting device (14) constructed as described above are applied to the image data processing device (computer) connected to the detecting device (14) via an interface, so that the identifying mark was read from the fluorescent image of the sample contact lens, and compared with the prepared reference data. The identifying mark read from the fluorescent image was confirmed to be identical with the reference data. The fluorescent image of the sample contact lens taken by the detecting device (14) is shown in FIG. 6.

As a comparative example, the sample contact lens was directly photographed by using a device similar to the device (14) while the lens was illuminated with a visible light. The obtained image of the lens is shown in FIG. 7.

Figure 6:
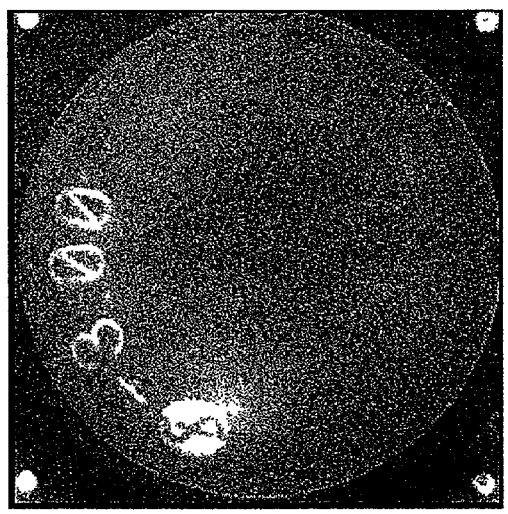
FIG. 6 is a fluorescent image of a contact lens with the identifying marks, which is taken in Example 1 according to the present invention.
Figure 7:
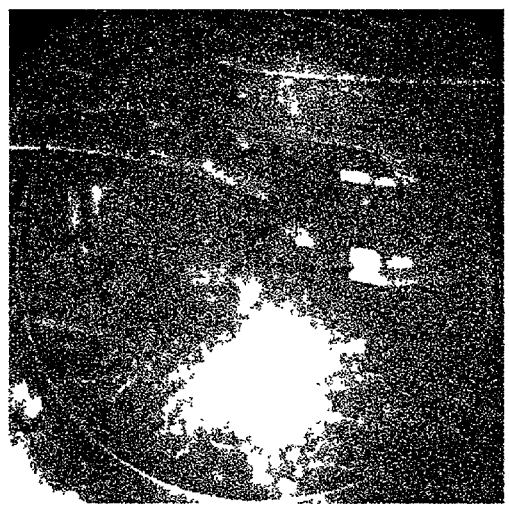
FIG. 7 is an image of a contact lens with the identifying marks, which is taken in Example 1 as a comparative example.

As is apparent from FIGS. 6 and 7, the identifying mark is represented by the fluorescent image of the lens with a higher degree of clarity than the image of the lens which is directly taken by a camera, whereby the identifying mark can be effectively recognized.

According to the present method of reading the identifying mark formed in the ophthalmic lens, the identifying mark, which is engraved with the laser radiation, for instance, and which is generally difficult to be recognized by a visual inspection, is clearly represented by the fluorescent image, so that the identifying mark formed in the ophthalmic lens can be easily and effectively recognized.

Example 2

Initially, there were prepared, as sample lenses, a new toric lens ("MENICON 72 TORIC LENS" available from Menicon Co., Ltd., Japan) and a new bifocal lens ("MENIFOCAL SOFT 72" available from Menicon Co., Ltd., Japan) having the respective specifications described below.

MENICON 72 TORIC LENS
    base curve: 8.70 mm optical power: −3.00 diameter: 14.0
        mm additional power: −1.75 axis: 180

MENIFOCAL SOFT 72
    base curve: 8.10 optical power −3.00 diameter: 13.5 mm
        additional power: +3.00 axis: −30

The thickness of each of these two sample lenses was measured by using a thickness measuring device described below.

Thickness Measuring Device

ORCA AQUACOSMOS package available from "KABUSHIKI KAISHA HAMAMATSU PHOTONICS, Japan
    image-taking device:    digital CCD camera (C-4742-95-12NR)
                                  F mount lens (f=55 mm, F2.8S)
    image analyzing device:    image data processing device
                                  (C7746-43E)
    image analyzing software:    AQUACOSMOS BASIC
                                  SOFTWARE (U 7501)
Excitation light source: mercury-xenon lamp 200W
Optical filter:
    <excitation light source>
        330-380UV excitation filter
    <image-taking device>
        sky light filter
           (cut-off filter adapted to inhibit transimission of a light
           whose wavelength is not larger than 390 nm) and
        400 absorption filter
           (cut-off filter adapted to inhibit transmission of a light
           whose wavelength is not larger than 400 nm)

Each of the sample lenses was immersed in a predetermined amount of a saline solution accommodated in a blister case (40) with its base curved surface facing upward, as shown in FIG. 2. The blister case (40) accommodating each sample contact lens therein was placed on a stage of the detecting device (14) constituted by the digital CCD camera (22) equipped with the F mount lens (20).

The excitation light was applied toward the upper surface of each sample lens, and the self-fluorescent light emitted from the lens by the exposure to the excitation light was detected on the upper side of the lens. As the electromagnetic radiation emitting device (10), the mercury-xenon lamp (200 W) as used in the above Example 1 was used. The mercury-xenon lamp is equipped with the optical filter similar to that described with respect to the above Example 1. The detecting device (14) is equipped with the optical filters similar to those described above with respect to the above Example 1.

Figure 10:
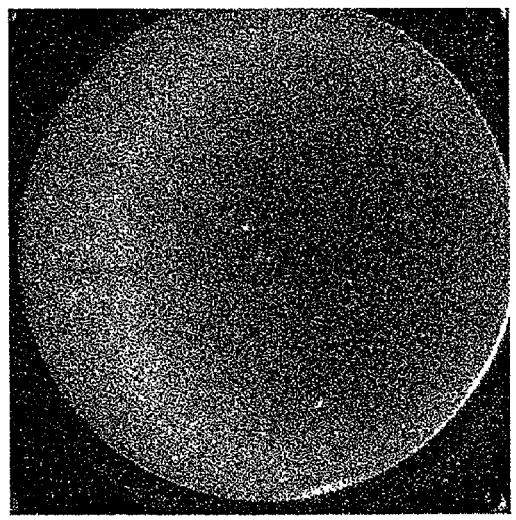
FIG. 10 is a fluorescent image of a toric lens taken in Example 2 according to the present invention.
Figure 11:
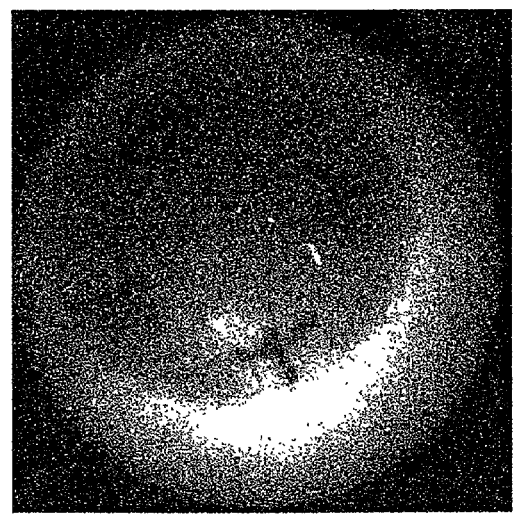
FIG. 11 is a fluorescent image of a bifocal lens taken in Example 2 according to the present invention.

The fluorescent image taken by the detecting device (14) constructed as described above is applied to the image data processing device (computer) connected to the detecting device (14) via an interface, so that the thickness of the lens at its geometric center portion (corresponding to one pixel) in a direction of its optical axis was obtained. The result of the measurement for each sample lens is indicated in the following Table 2, together with the number (n) of measurement and the standard deviation ($\sigma$). The fluorescent images (in 256 gradation steps) of the sample lenses, i.e., the toric lens and the bifocal lens, are indicated in the respective black-and-white pictures, as shown in FIGS. 10 and 11.

The reference data used in obtaining the thickens of each sample lens were determined by obtaining, under the same condition as that for measuring the thickness of each sample lens, the luminance values of a plurality of plates formed of the same material as the material of each sample lens and having different thickness values. The relationship between the luminance values and the thickness values of each sample lens is represented by a calibration curve which is obtained by second-order least square approximation. The obtained calibration curve for each sample lens is stored in the hard disc of the computer. The calibration curves for the two sample lenses, i.e., the toric lens and the bifocal lens, are represented by the following equations (1) and (2), respectively.

$$y=0.0002x^2+0.0108x-0.0364 \text{ (correlation function=0.95)} \quad \text{<equation (1)>}$$

$$y=0.00006x^2+0.0016x+0.0326 \text{ (correlation function=0.95)} \quad \text{<equation (2)>}$$

As a comparative example, the center thickness of each sample lens was measured by using a low-contact-force thickness measuring device ("LITEMATIC VL-50" available from KABUSHIKI KAISHA MITSUTOYO, Japan). The results of the measurement are also indicated in the TABLE 2. In the following TABLE 2, the design value of the center thickness for each sample lens is also indicated.

TABLE 2

|  | toric lens | bifocal lens |
| --- | --- | --- |
| Sample lens according to the present invention | 0.122 mm ($\sigma$ = 0.0160, n = 5) | 0.248 mm ($\sigma$ = 0.097, n = 5) |
| Sample lens as comparative example | 0.125 mm | 0.251 mm |
| Design value | 0.120 mm | 0.243 mm |

As is apparent from the results indicated in the TABLE 2, the center thickness values obtained for the sample lenses according to the present invention are substantially equal or close to the respective design values. Thus, it is understood that the thickness of the toric lens and bifocal lens can be measured with an accuracy which is equal to or higher than that in measuring the thickness by using the conventional low-contact-force thickness measuring device. According to the present method, the thickness of the ophthalmic lens can be accurately measured without a risk of damaging the ophthalmic lens.

Example 3

Initially, there were prepared, as sample lenses, a new toric lens (an astigmatism correction contact lens "MENICON 72 TORIC LENS" available from Menicon Co., Ltd., Japan) and a new contact lens (a presbyopia correction contact lens "MENIFOCAL SOFT 72" available from Menicon Co., Ltd., Japan) having the respective specifications described below.

MENICON 72 TORIC LENS
  base curve: 8.70 mm optical power: −3.00 diameter: 140 mm additional power: −1.75 axis: 180

MENIFOCAL SOFT 72
  base curve: 8.10 mm optical power −3.00 diameter: 13.5 mm additional power: +3.00 axis: −30

The angular position of each of these two sample lenses was detected by using an angular position detecting device described below.

Angular Position Detecting Device

ORCA AQUACOSMOS package available from "KABUSHIKI KAISHA HAMAMATSU PHOTONICS, Japan
  image-taking device: digital CCD camera (C-4742-95-12NR) F mount lens (f=55 mm, F2.8S)
  image analyzing device: image data processing device (C7746-43E)
  image analyzing software: AQUACOSMOS BASIC SOFTWARE (U 7501)
Excitation light source: mercury-xenon lamp 200W
Optical filter:
  <excitation light source>
    330–380UV excitation filter
  <image-taking device>
    sky light filter
      (cut-off filter adapted to inhibit transimission of a light whose wavelength is not larger than 390 nm) and
    400 absorption filter
      (cut-off filter adapted to inhibit transmission of a light whose wavelength is not larger than 400 nm)

Each of the sample lenses was immersed in a predetermined amount of a saline solution accommodated in a blister case (40) with its base curved surface facing upward, as shown in FIG. 2. The blister case (40) accommodating each sample contact lens therein was placed on a stage of the detecting device (14) constituted by the digital CCD camera (22) equipped with the F mount lens (20).

The excitation light was applied toward the upper surface of each sample lens, and the self-fluorescent light emitted from the lens by the exposure to the excitation light was detected on the upper side of the sample lens. As the electromagnetic radiation emitting device (10), the mercury-xenon lamp (200 W) as used in the above Example 1 was used. The mercury-xenon lamp is equipped with the optical filter similar to that described with respect to the above Example 1. The detecting device (14) is equipped with the optical filters similar to those described above with respect to the above Example 1.

The image data representative of the fluorescent image taken by the detecting device (14) constructed as described above are applied to the image data processing device (computer) connected to the detecting device (14) via an interface, so that the reference radial direction and the angle a defined by the reference radial direction and the horizontal axis L of the lens are detected. The fluorescent images of the sample lenses taken by the detecting device (14) are shown in FIGS. 15 and 16.

Figure 15:
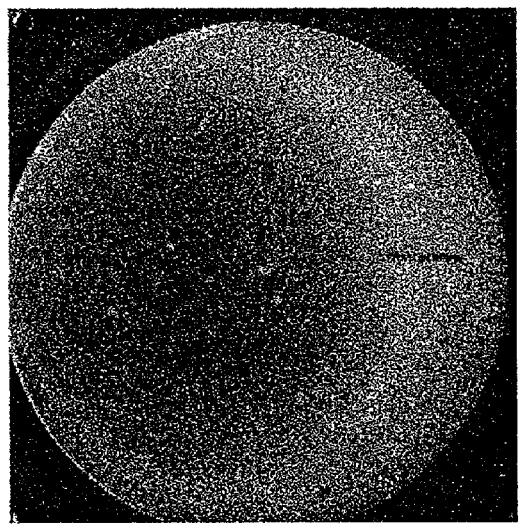
FIG. 15 is a fluorescent image of an astigmatism correction contact lens (toric lens) which is taken in Example 3 according to the present invention.
Figure 16:
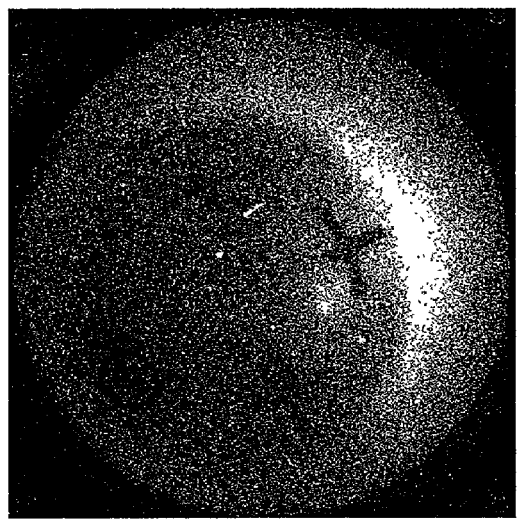
FIG. 16 is a fluorescent image of a presbyopia correction contact lens (bifocal lens) which is taken in Example 3 according to the present invention.

It is apparent from FIGS. 15 and 16 that the self-fluorescent image of each sample lens exhibits high luminance values at its thickest circumferential portion corresponding to the prism ballast, for thereby permitting an easy detection of the reference radial direction of the lens.

According to the present method, the angular position of the ophthalmic lens can be easily and quickly detected with a high degree of accuracy without a risk of causing detecting errors of the individual workers and without requiring a relatively long detecting time.

It is to be understood that the present invention may be embodied with various other changes, modifications and improvements, such as those described in the SUMMARY OF THE INVENTION, which may occur to those skilled in the art, without departing from the spirit and scope of the invention defined in the following claims:

What is claimed is:

1. A method of reading an identifying mark in the form of a character, a figure, or a symbol, which is formed in a predetermined portion of a surface of an ophthalmic lens and which identifies said ophthalmic lens, comprising the steps of:

irradiating said ophthalmic lens with an excitation light so that a self-fluorescent light is emitted from said ophthalmic lens;

taking a fluorescent image of said ophthalmic lens while said ophthalmic lens is emitting said self-fluorescent light;

obtaining information on said ophthalmic lens by reading said identifying mark formed in said ophthalmic lens on the basis of said fluorescent image.

2. A method according to claim 1, further comprising a step of judging whether the obtained information is identical with prepared reference information.

3. A method according to claim 1, wherein said step of irradiating said ophthalmic lens with an excitation light and said step of taking a fluorescent image are effected with said ophthalmic lens being immersed in a liquid medium accommodated in a container.

4. A method according to claim 1, wherein said step of taking a fluorescent image of said ophthalmic lens is effected by using a CCD camera.

5. A method according to claim 1, wherein said excitation light is a UV light having a wavelength in a range of 200–400 nm.

6. A method according to claim 1, wherein said self-fluorescent light has a wavelength in a range of 340–470 nm.

* * * * *